United States Patent
Kohara et al.

(10) Patent No.: US 11,051,496 B2
(45) Date of Patent: *Jul. 6, 2021

(54) UROKINASE-TYPE PLASMINOGEN ACTIVATOR TRANSGENIC MOUSE

(71) Applicants: TOKYO METROPOLITAN INSTITUTE OF MEDICAL SCIENCE, Tokyo (JP); CHUGAI SEIYAKU KABUSHIKI KAISHA, Tokyo (JP); PHOENIXBIO CO., LTD., Higashihiroshima (JP)

(72) Inventors: Michinori Kohara, Tokyo (JP); Koichi Jishage, Gotemba (JP); Yosuke Kawase, Gotemba (JP); Chise Mukaidani, Higashihiroshima (JP); Hiroki Oshita, Higashihiroshima (JP); Satoko Hamamura, Higashihiroshima (JP)

(73) Assignees: TOKYO METROPOLITAN INSTITUTE OF MEDICAL SCIENCE, Tokyo (JP); CHUGAI SEIYAKU KABUSHIKI KAISHA, Tokyo (JP); PHOENIXBIO CO., LTD., Higashihiroshima (JP)

( * ) Notice: Subject to any disclaimer, the term of this patent is extended or adjusted under 35 U.S.C. 154(b) by 202 days.

This patent is subject to a terminal disclaimer.

(21) Appl. No.: 15/934,520

(22) Filed: Mar. 23, 2018

(65) Prior Publication Data

US 2019/0335724 A1  Nov. 7, 2019

Related U.S. Application Data

(63) Continuation of application No. 14/397,091, filed as application No. PCT/JP2013/062806 on Apr. 25, 2013, now Pat. No. 9,955,675.

(30) Foreign Application Priority Data

Apr. 27, 2012 (JP) ................................ 2012-102814

(51) Int. Cl.
    A01K 67/027   (2006.01)
    C12N 9/72     (2006.01)
    C12N 15/85    (2006.01)
    C12N 15/877   (2010.01)
    G01N 33/50    (2006.01)

(52) U.S. Cl.
    CPC ...... A01K 67/0275 (2013.01); A01K 67/0271 (2013.01); C12N 9/6462 (2013.01); C12N 15/8509 (2013.01); C12N 15/8775 (2013.01); G01N 33/5067 (2013.01); G01N 33/5088 (2013.01); A01K 2207/12 (2013.01); A01K 2207/15 (2013.01); A01K 2217/052 (2013.01); A01K 2217/15 (2013.01); A01K 2217/206 (2013.01); A01K 2227/105 (2013.01); A01K 2267/035 (2013.01); A01K 2267/0337 (2013.01); C12N 2015/8581 (2013.01); Y10T 436/146666 (2015.01)

(58) Field of Classification Search
    CPC .................................................. A01K 67/0275
    See application file for complete search history.

(56) References Cited

U.S. PATENT DOCUMENTS

| | | | |
|---|---|---|---|
| 6,509,514 B1 | 1/2003 | Kneteman et al. | |
| 2003/0115616 A1 | 6/2003 | Kneteman et al. | |
| 2003/0217373 A1 | 11/2003 | Green et al. | |
| 2007/0101443 A1 | 5/2007 | Daly | |

FOREIGN PATENT DOCUMENTS

| JP | 2008-22853 A | 2/2008 |
|---|---|---|
| JP | 2009-55911 A | 3/2009 |

(Continued)

OTHER PUBLICATIONS

Tateno et al. (2004, American J. Pathology, vol. 165(3), pp. 901-912). (Year: 2004).*

(Continued)

*Primary Examiner* — Thaian N. Ton
*Assistant Examiner* — David A. Montanari
(74) *Attorney, Agent, or Firm* — Birch, Stewart, Kolasch & Birch, LLP

(57) ABSTRACT

The present invention provides a mouse with liver damage, having a high degree of damage against the mouse's original hepatocytes while having a uPA gene in a heterozygous form, and a method for efficiently preparing the mouse. Specifically, the method for preparing a mouse with liver damage having the uPA gene in a heterozygous form comprises the following steps of:

(i) transforming mouse ES cells with a DNA fragment containing a liver-specific promoter/enhancer and cDNA that encodes a urokinase-type plasminogen activator operably linked under the control thereof;

(ii) injecting the transformed mouse ES cells obtained in step (i) into a host embryo;

(iii) transplanting the host embryo obtained in step (ii) via the injection of the ES cells into the uterus of a surrogate mother mouse, so as to obtain a chimeric mouse; and (iv) crossing the chimeric mice obtained in step (iii), so as to obtain a transgenic mouse in which the DNA fragment is introduced in a heterozygous form.

11 Claims, 13 Drawing Sheets
(1 of 13 Drawing Sheet(s) Filed in Color)
Specification includes a Sequence Listing.

(56) References Cited

FOREIGN PATENT DOCUMENTS

| JP | 2010-136726 A | 6/2010 |
|----|---------------|--------|
| WO | WO 2010/082385 A1 | 7/2010 |

OTHER PUBLICATIONS

Angulo, P., M.D., "Nonalcoholic Fatty Liver Disease," N. Engl. J. Med. (Apr. 18, 2002), vol. 16, pp. 1221-1231.

English translation of International Preliminary Report on Patentability dated Oct. 27, 2014, in PCT International Application No. PCT/JP2013/062806.

English translation of International Search Report dated Jul. 16, 2013, in PCT International Application No. PCT/JP2013/062806.

Haridass et al., "Repopulation Efficiencies of Adult Hepatocytes, Fetal Liver Progenitor Cells, and Embryonic Stem Cell-Derived Hepatic Cells in Albumin-Promoter-Enhancer Urokinase-Type Plasminogen Activator Mice," Am. J. Pathol. (Oct. 2009), vol. 175, No. 4, pp. 1483-1492.

Lutgehetmann et al., "Humanized Chiimeric uPA Mouse Model for the Study of Hepatitis B and D Virus Interactions and Preclinical Drug Evaluation," Hepatology (2012), vol. 55, pp. 685-694.

Meuleman, P. and G. Leroux-Roels, "The human liver-uPA-SCID mouse: A model for the evaluation of antiviral compounds against HBV and HCV," Antiviral Research (2008), vol. 80, pp. 231-238.

Oshita et al., "Development of Chimeric mice with human hepatocytes suitable for long-term studies with the use of cDNA-uPA/SCID mice as hosts," Conference for Laboratory Animal Sciences and Technologies Kyushu 2012 (May 1, 2012), p. 250, upper part (P107-S1), with English translation.

Rhim et al., "Complete reconstitution of mouse liver with xenogenic hepatocytes," Proc. Natl. Acad. Sci. USA (May 1995), vol. 92, pp. 4942-4946.

Sandgren et al., "Complete Hepatic Regeneration after Somatic Deletion of an Albumin-Plasminogen Activator Transgene," Cell (Jul. 26, 1991), vol. 66, pp. 245-256.

Suemizu et al., "Establishment of a humanized model of liver using NOD/Shi-scid IL2Rgnull mice," Biomedical and Biophysical Research Communications (2008), vol. 377, pp. 248-252.

Tateno et al., "Near Completely Humanized Liver in Mice Shows Human-Type Metabolic Responses to Drugs," Am. J. Pathol. (Sep. 2004), vol. 165, No. 3, pp. 901-912.

Bioweb: RNA processing pathway. Online 2012.

Computational Genomics, Biology and Computing 2006.

Dandri et al., "Repopulation of Mouse Liver With Human Hepatocytes and In Vivo Infection With Hepatitus B Virus," Hepatology, vol. 33, No. 4, XP009027503, Apr. 2001, pp. 981-988.

Extended European Search Report dated Dec. 7, 2015, for European Application No. 13780731.9.

Kawakara et al. Liver Transplant 2010; 16:974-82.

Mercer et al. Nat Med 2001; 7:927-33.

* cited by examiner

Fig. 3

| Line | uPA Tg | Body weight (g) | Liver weight (g) | Liver/ body weight (%) | ALT (Karmen unit) | | | |
|---|---|---|---|---|---|---|---|---|
| | | | | | 3W | 4W | 6W | 8W |
| 2C7 | + | 19.20 | 1.07 | 5.52 | 32.29 | 47.60 | 57.10 | 97.35 |
| | - | 25.23 | 1.14 | 4.41 | 17.11 | 14.85 | 18.73 | 12.29 |
| 1C2 | + | 18.40 | 0.90 | 4.87 | 31.54 | 33.39 | 62.83 | 72.76 |
| | - | 25.13 | 1.28 | 5.12 | 23.79 | 24.76 | 32.50 | 26.90 |
| 1D3 | + | 26.06 | 1.31 | 5.05 | 37.99 | 30.57 | 41.70 | 36.86 |
| | - | 30.49 | 1.34 | 4.40 | 17.34 | 14.12 | 17.99 | 21.59 |

1C2

1C2 Homo

N1R1-2 (10.8 mg/mL)  N1R1-4 (8.4 mg/mL)

N1R1-1 (6.1 mg/mL)  N1R1-3 (2.2 mg/mL)

1C2 Hetero

N1R1-9 (7.8 mg/mL)  N1R1-10 (2.1 mg/mL)

2C7 Homo

N2R1-1 (11.7 mg/mL)

1C2

2C7 of the uPA gene is observed. Since mouse cells lacking the uPA gene regenerate hepatocytes again, it has been difficult

UROKINASE-TYPE PLASMINOGEN ACTIVATOR TRANSGENIC MOUSE

CROSS-REFERENCE TO RELATED APPLICATIONS

This application is a Continuation of copending application Ser. No. 14/397,091, filed on Oct. 24, 2014, which is the National Phase under 35 U.S.C. § 371 of International Application No. PCT/JP2013/062806, filed on Apr. 25, 2013, which claims the benefit under 35 U.S.C. § 119(a) to Patent Application No. 2012-102814, filed in Japan on Apr. 27, 2012, all of which are hereby expressly incorporated by reference into the present application.

TECHNICAL FIELD

The present invention relates to a mouse with liver damage, which is prepared by introducing a DNA fragment that contains a liver-specific promoter/enhancer and cDNA encoding an urokinase-type plasminogen activator operably linked under the control thereof, into ES cells and then using the ES cells, wherein the DNA fragment is introduced in a heterozygous form.

BACKGROUND ART

Experimentation using human cells is generally desired to study human diseases. In particular, studies of diseases, in which many drug-metabolizing enzymes confirmed to have species specificity, viruses, the hosts of which are limited to humans, and the like are involved, require to use human cells, and particularly human hepatocytes. However, the supply of human hepatocytes is limited and in vitro proliferation of human hepatocytes while keeping their differentiation status is very difficult. The use of in vivo environment is relatively efficient for the proliferation of human hepatocytes. Specifically, a gene accelerating the death of mouse hepatocytes is introduced into mice that have been produced from immunodeficient mice as the genetic background to produce transgenic mice, human hepatocytes are transplanted into the transgenic mice, and then human hepatocytes are proliferated. In this manner, the replacement of most mouse hepatocytes by human hepatocytes has been attempted.

Liver disease caused by the infection of human liver with viruses is a disease difficult to treat in recent years in medical practice. Animal species susceptible to these viruses that infect human hepatocytes are limited to humans and chimpanzees. Tests using human hepatocytes are required to develop remedies against these viral infections. Also, hepatocytes play important roles in drug metabolism. Elucidation of the metabolic pathways of individual drugs in humans is considered to lead to the development of new pharmaceutical products. However, species specificity is present in many drug-metabolizing enzymes, and thus elucidation of the drug metabolic pathways in humans requires to conduct tests using human hepatocytes.

Regarding Hepatitis C virus (HCV), about 1500,000 carriers of Hepatitis C virus (HCV carriers), and about 400,000 to 500,000 patients other than these carriers are estimated to be treated in Japan. The number of chronic hepatitis C patients receiving interferon administration is said to be annually 30,000 to 40,000. In these days, new antiviral agents targeting various sites of viral genome are under development. However, the advancement thereof is significantly inhibited because of the lack of reliable HCV animal models with high reproducibility. This can be said for not only HCV, but also other types of viral hepatitis such as hepatitis type B virus (HBV). Hosts for these viruses are only humans and chimpanzees. Therefore, development of small model animals produced by replacing human hepatocytes by a host's hepatocytes is desired for large-scale development and study of antiviral agents using animals.

Fatty liver is developed due to the accumulation of neutral fat in the liver. In recent years, the incidence of non-alcoholic steatohepatitis (NASH) that is hepatitis resulting from the accumulation of fat in the liver is increasing. This disease may proceed to diseases with poor prognosis such as chronic hepatitis, hepatic cirrhosis, and hepatocellular carcinoma. Meanwhile, the absence of effective remedies against such liver diseases has been suggested (Non-patent Literature 1). The development of such remedies also requires the presence of optimum animal models.

If the use of model animals having human hepatocytes as a result of replacement becomes possible for the study of the above diseases, this will contribute to many studies for drug development. However, the preparation of the model animals requires efficient proliferation of human hepatocytes after transplantation thereof into host animals and successful replacement thereof by the host's hepatocytes.

Several examples of transplantation of human hepatocytes into transgenic mice have been reported, wherein human hepatocytes are transplanted into the transgenic mice in which an urokinase-type plasminogen activator (hereinafter, referred to as "uPA") gene is expressed liver-specifically, so as to damage mouse hepatocytes. uPA transgenic mice prepared using the genomic sequence of uPA (Non-patent Literature 2) and uPA transgenic mice prepared using the cDNA of uPA (Non-patent Literature 3) have been reported. All of these uPA transgenic mice are required to have the uPA gene in a homozygous form, since the engraftment of transplanted human hepatocytes is difficult when the mice have the uPA gene in a heterozygous form. However, the preparation of transgenic mice having the uPA gene in a homozygous form requires at least two generations and at least 6 months. Moreover, homozygous mice are obtained in a proportion of about only 25% with respect to the total number of the thus obtained mice. It has been difficult to prepare transgenic mice having a large quantity of the uPA gene in a homozygous form within a short period. It has also been difficult to prepare a cross-bred line with another transgenic mouse due to a similar reason. Moreover, in transgenic mice produced using a conventional uPA genomic sequence, the recombination of the uPA gene introduced into the liver takes place over time, and the loss for human hepatocytes to engraft after transplantation thereof into heterozygous mice. Furthermore, in homozygous mice, mouse hepatocytes are regenerated due to the loss of the uPA gene, and thus a gradual decrease in human hepatocytes that have engrafted is frequently observed among mice. Hence, uPA transgenic mice that can be produced efficiently in large quantity and enables easy preparation of a cross-bred line with another transgenic mouse have been desperately desired in the art.

PRIOR ART LITERATURE

Non-Patent Literature

Non-patent Literature 1 N Engl J Med. 346:1221-31 (2002)
Non-patent Literature 2 Cell 66: 245-256 (1991)
Non-patent Literature 3 BBRC 377: 248-252 (2008)

SUMMARY OF THE INVENTION

The present invention provides mice with liver damage, having a high degree of damage to the original mouse hepatocytes while having the uPA gene in a heterozygous form, and a method for efficiently preparing the mice.

As a result of intensive studies to achieve the above object, the present inventors have discovered that transgenic mice having a high degree of damage to the original mouse hepatocytes while having the uPA gene in a heterozygous form can be efficiently prepared by introducing a DNA fragment that contains a liver-specific promoter/enhancer and cDNA encoding uPA operably linked under the control thereof, into mouse ES cells and then using the ES cells. The present inventors have also discovered that no or almost no loss of the introduced uPA gene takes place over time in the transgenic mice.

The present inventors have further discovered that human hepatocytes transplanted into immunodeficient mice with liver damage can engraft, which are prepared using the above transgenic mice.

The present invention is based on these findings.

Specifically, the present invention encompasses the following [1] to [14].

[1] A method for preparing a mouse with liver damage, which has an uPA gene in a heterozygous form, comprising the following steps of:
(i) transforming mouse ES cells with a DNA fragment containing a liver-specific promoter/enhancer and cDNA that encodes a urokinase-type plasminogen activator operably linked under the control thereof;
(ii) injecting the transformed mouse ES cells obtained in step (i) into a host embryo;
(iii) transplanting the host embryo obtained in step (ii) via the injection of the ES cells into the uterus of a surrogate mother mouse, so as to obtain a chimeric mouse; and
(iv) crossing the chimeric mice obtained in step (iii), so as to obtain a transgenic mouse in which the DNA fragment is introduced in a heterozygous form.

[2] The method of [1], further comprising step (v) of obtaining a transgenic mouse in which the serum ALT level of the 2- to 3-week-old transgenic mouse is 30 (Karmen unit) or more.

[3] The method of [1] or [2], wherein the liver-specific promoter is an albumin promoter.

[4] A mouse with liver damage prepared by the method of [1] to [3] and a portion thereof.

[5] An immunodeficient mouse with liver damage, which is obtained by crossing the mouse with liver damage of [4] with a SCID mouse.

[6] A method for preparing a chimeric mouse characterized by having a chimeric liver containing human hepatocytes, comprising transplanting human hepatocytes into the immunodeficient mouse with liver damage of [5].

[7] A chimeric mouse prepared by the method of [6], which has a chimeric liver containing human hepatocytes.

[8] A chimeric mouse, which is immunodeficient, has a DNA fragment containing a liver-specific promoter/enhancer and cDNA that encodes a urokinase-type plasminogen activator operably linked under the control thereof, in a heterozygous form, and has a chimeric liver containing human hepatocytes.

[9] The chimeric mouse of [7] or [8], wherein human hepatocytes account for at least 10% of all hepatocytes in the chimeric liver.

[10] The chimeric mouse of [7] or [8], wherein the human hepatocytes retain their functions and properties for at least 2 weeks in the chimeric liver.

[11] A method for screening for a substance that affects human liver functions, comprising the following steps (a) to (c) of:
(a) administering a test substance to the chimeric mouse of any one of [7] to [10];
(b) measuring one or more values selected from the group consisting of the human albumin concentration, the body weight curve, the liver-weight-to-body-weight ratio, the total albumin level, the total protein level, the ALT level, the AST level, and the total bilirubin level in the chimeric mouse to which the test substance is administered in (a); and
(c) selecting a test substance that causes an increase or a decrease in any one or more of the human albumin concentration, the body weight curve, the liver-weight-to-body-weight ratio, the total albumin level, the total protein level, the ALT level, the AST level, and the total bilirubin level measured in (b), compared with the human albumin concentration, the body weight curve, the liver-weight-to-body-weight ratio, the total albumin level, the total protein level, the ALT level, the AST level, and the total bilirubin level of the chimeric mouse to which no test substance is administered.

[12] A method for evaluating the toxicity of a test substance against human hepatocytes, comprising the following steps (a) to (c) of:
(a) administering a test substance to the chimeric mouse of any one of [7] to [10];
(b) measuring one or more values selected from the group consisting of the human albumin concentration, the body weight curve, the liver-weight-to-body-weight ratio, the total albumin level, the total protein level, the ALT level, the AST level, and the total bilirubin level in the chimeric mouse to which the test substance is administered in (a); and
(c) evaluating the effect of the test substance on human hepatocytes using, as an indicator, an increase or a decrease in any one or more of the human albumin concentration, the body weight curve, the liver-weight-to-body-weight ratio, the total albumin level, the total protein level, the ALT level, the AST level, and the total bilirubin level measured in (b), compared with the human albumin concentration, the body weight curve, the liver-weight-to-body-weight ratio, the total albumin level, the total protein level, the ALT level, the AST level, and the total bilirubin level of the chimeric mouse to which no test substance is administered.

[13] A method for screening for a substance effective for treatment of viral hepatitis, comprising the following steps (a) to (d) of:
(a) inoculating a hepatitis virus into the chimeric mouse of any one of [7] to [10];
(b) administering a test substance to the chimeric mouse inoculated with the hepatitis virus in (a);
(c) measuring one or more values selected from the group consisting of the human albumin concentration, the body weight curve, the liver-weight-to-body-weight ratio, the total albumin level, the total protein level, the ALT level, the AST level, the total bilirubin level, the viral load, and the amount of a virus-derived protein of the chimeric mouse to which the test substance is administered in (b); and
(d) selecting a test substance causing a change in any one or more of the human albumin concentration, the body weight curve, the liver-weight-to-body-weight ratio, the total albumin level, the total protein level, the ALT level, the AST level, the total bilirubin level, the viral load, and the amount of a virus-derived protein measured in (c), compared with the human albumin concentration, the body weight curve, the liver-weight-to-body-weight ratio, the total albumin level, the total protein level, the ALT level, the AST level, the total bilirubin level, the viral load, and the amount of a virus-derived protein in the chimeric mouse to which no test substance is administered.

[14] The method of [13], wherein the hepatitis virus is hepatitis type A virus, hepatitis type B virus, hepatitis type C virus, hepatitis type D virus, or hepatitis type E virus.

This description includes all or part of the contents as disclosed in the description and/or drawings of Japanese Patent Application No. 2012-102814, from which the present application claims the priority.

BRIEF DESCRIPTION OF THE DRAWINGS

The patent or application file contains at least one color drawing. Copies of this patent application publication with color drawing will be provided by the USPTO upon request and payment of the necessary fee.

FIG. 3 shows the results of measuring, the ALT levels and so on in uPA transgenic mice prepared via ES cells.

FIG. 8-1 shows human albumin concentrations in mouse blood (left) before HCV inoculation and each viral copy number (right) in mouse serum after inoculation of chimeric mice prepared using #1C2 homozygous and #1C2 heterozygous mice. Solid lines denote homozygous mice and dotted lines denote heterozygous mice.

FIG. 8-2 shows human albumin concentrations in mouse blood (left) before HBV inoculation and each viral copy numbers (right) in mouse serum after inoculation of chimeric mice prepared using #1C2 homozygous and #1C2 heterozygous mice. Solid lines denote homozygous mice and dotted lines denote heterozygous mice.

FIG. 9-1 shows human albumin concentrations in mouse blood (left) before HCV inoculation and HCV copy numbers (right) in mouse serum after inoculation of chimeric mice prepared using #2C7 homozygous mice.

FIG. 9-2 shows human albumin concentrations in mouse blood (left) before HBV inoculation and HBV copy numbers (right) in mouse serum after inoculation of chimeric mice prepared using #2C7 homozygous mice.

MODES FOR CARRYING OUT THE INVENTION

Figure 1:
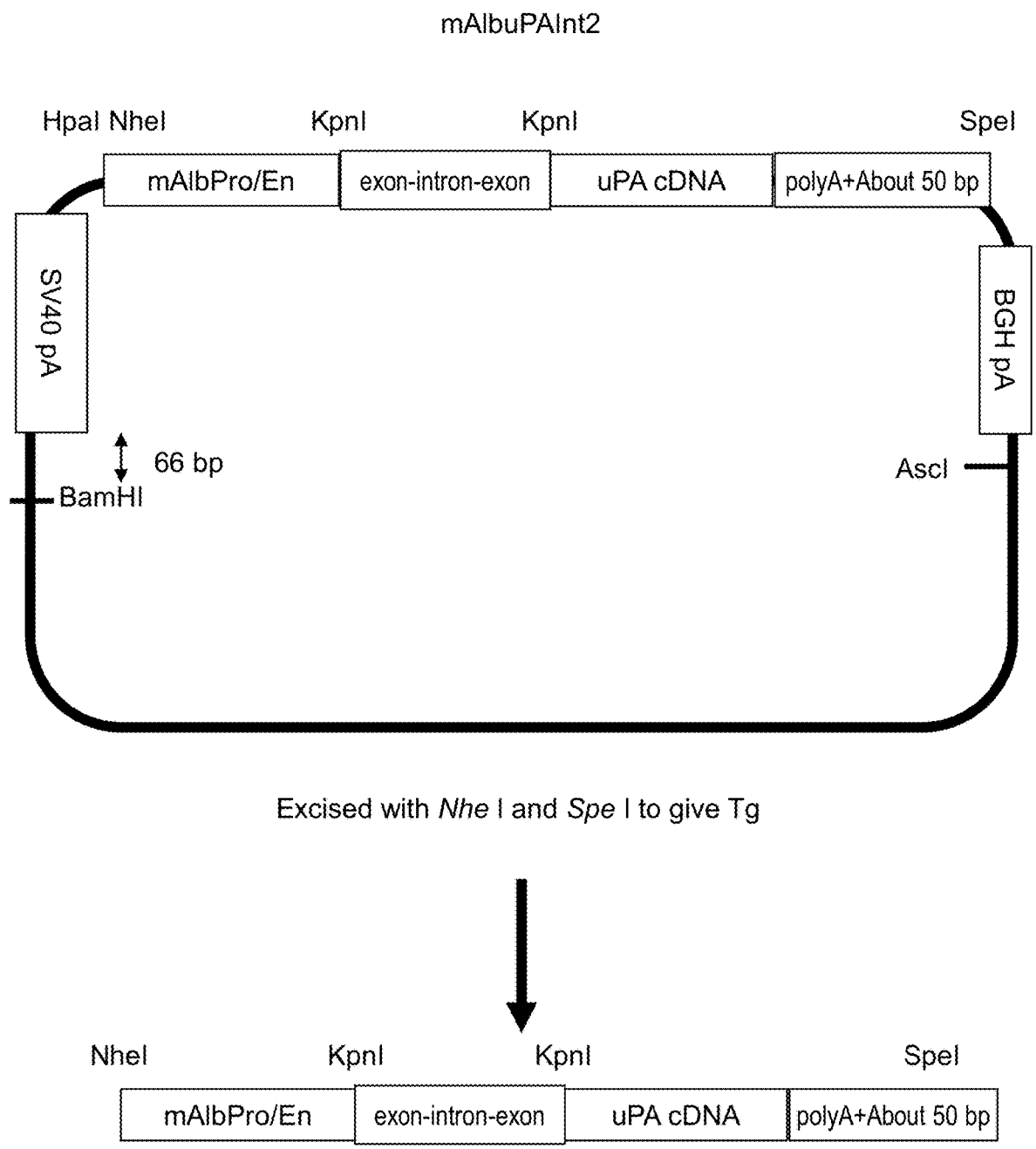
FIG. 1 is a schematic view showing an uPA gene insertion vector for fertilized eggs, "mAlb uPAInt2". SV40 pA: SV40 polyA signal; mAlbPro/En: mouse albumin enhancer/promoter; uPA cDNA: the ORF portion of mouse uPA; exon-intron-exon: the $2^{nd}$ exon, intron, and the $3^{rd}$ exon of rabbit β globin; polyA+About 50 bp: polyA signal in the $3^{rd}$ exon of rabbit β globin.

The present invention will be described below in detail.

The mouse with liver damage of the present invention has a DNA fragment containing a liver-specific promoter/enhancer and cDNA that encodes a urokinase-type plasminogen activator operably linked under the control thereof, in a heterozygous form, whereby uPA is expressed liver-specifically, and at least 20%, at least 30%, at least 40%, at least 50%, at least 60%, at least 70%, at least 80%, at least 90%, at least 95% or more of original mouse liver cells (particularly, hepatocytes) are damaged, the proliferation thereof is suppressed, and/or the cells are necrotized.

The mouse with liver damage of the present invention has a high degree of damage against original mouse hepatocytes while having the uPA gene in a heterozygous form, and thus are not required to have the uPA gene in a homozygous form unlike conventionally known uPA transgenic mice.

The mouse with liver damage of the present invention can be prepared on the basis of a conventionally known method for preparing transgenic animals (Proc. Natl. Acad. Sci. U.S.A. 77: 7380-7384 (1980)) by introducing a DNA fragment containing a liver-specific promoter/enhancer and cDNA that encodes uPA operably linked under the control thereof into mouse ES cells and then using the thus obtained ES cells.

The term "promoter/enhancer" refers to DNA having a sequence capable of providing the functions of both the promoter and the enhancer.

Examples of a "liver-specific promoter" include, but are not particularly limited to, as long as it can induce the expression of a gene ligated to the 3' side in a liver-specific manner, an albumin promoter, an α-fetoprotein promoter, an $α_1$-anti-trypsin promoter, a transferrin transthyretin promoter, a serum amyloid A promoter, a transthyretin promoter, and a hepatocyte nuclear factor 6 (HNF-6) promoter. A preferable example thereof is an albumin promoter.

The "liver-specific promoter/enhancer" may be any one of an endogenous promoter/enhancer, an exogenous promoter/enhancer, a promoter/enhancer of the same species, a promoter/enhancer of a different species, an artificial promoter/enhancer, as long as it enables the expression of a target gene liver-specifically. Preferably, a mouse-derived promoter/enhancer is used. A mouse-derived liver-specific promoter/enhancer is known in the art. For example, an albumin promoter/enhancer can be used. A mouse-derived albumin promoter/enhancer is known (Herbst R S et al, Proc Natl Acad Sci U.S.A. 1989 March; 86 (5): 1553-7; Heckel J L et al., Cell 1990 Aug. 10; 62(3): 447-56), and can be obtained by performing PCR using primers specific to the albumin promoter/enhancer and a mouse genomic library as a template.

uPA-encoding cDNA may be any one of endogenous cDNA, exogenous cDNA, cDNA of the same species, and cDNA of a different species. Preferably, mouse-derived cDNA is used. The uPA-encoding cDNA can be obtained by a general technique known by persons skilled in the art, specifically by performing reverse transcription PCR using RNA extracted from the liver as a template and primers specific to an uPA-encoding gene. The uPA-encoding gene was registered under Accession No. NM008873 in the above published database. In the present invention, the gene information can be used (in this Description, the uPA-encoding gene is represented by SEQ ID NO: 11). In addition, in the Description, the term "uPA gene" described in the present invention refers to uPA-encoding cDNA. These terms can be used interchangeably.

The term "a liver-specific promoter/enhancer and cDNA that encodes uPA operably linked under the control thereof" means that uPA-encoding cDNA is arranged so that uPA is expressed under the control of the liver-specific promoter/enhancer.

The DNA fragment containing a liver-specific promoter/enhancer and cDNA that encodes uPA operably linked under the control thereof is introduced into ES cells (embryonic stem cells).

The DNA fragment can be introduced into ES cells by a calcium phosphate method, an electrical pulse method, a lipofection method, an aggregation method, a microinjection method, a particle gun method, a DEAE-dextran method, or the like (examples thereof are not limited thereto).

ES cells prepared by introducing the DNA fragment can be cultured ex vivo, so that cells into which the DNA fragment has been introduced successfully and/or cells in which the introduced DNA fragment has not been lost can be screened for. Next, the thus obtained ES cells are injected into a host embryo, and preferably a mouse blastocyst, the resultant is transplanted into the uterine horn of a surrogate mother mouse for generation, and thus transgenic mice (chimeric mice) are born. As a surrogate mother mouse, in general, a female pseudopregnant mouse produced by crossing with a male mouse subjected to vasectomy is used.

The resulting transgenic mice (chimeric mice) are confirmed for the incorporation of the above DNA fragment and then crossed with wild-type mice for the birth of F1 mice. Among F1 mice that are born as a result of this crossing, mice having the above DNA fragment (heterozygote) in somatic cells are transgenic mice capable of transmitting the above DNA fragment to germ cells.

The mouse with liver damage of the present invention may be a mouse of any generation of the above transgenic mice, as long as the introduced DNA fragment is a heterozygote. The selection of a heterozygote can be tested by screening chromosomal DNA separated and extracted from the F1 mouse tail by Southern hybridization or a PCR method, for example.

Moreover, from the thus obtained transgenic mice, 2- to 3-week-old transgenic mice exhibiting the serum ALT (alanine aminotransferase) level of 30 (Karmen unit) or higher are selected. Preferably, 3-week-old or 4 week-old transgenic mice exhibiting the serum ALT level of 30 (Karmen unit) or higher, further preferably 6 week-old transgenic mice exhibiting the serum ALT level of 45, 50 or 55 (Karmen unit) or higher, particularly preferably 8-week-old transgenic mice exhibiting the serum ALT level of 60, 65, or 70 (Karmen unit) or higher are selected. A serum ALT level can be an indicator for the degree of liver damage. The higher the serum ALT level, the higher the degree of liver damage.

The above ES cells and blastocysts to be used for preparing the mouse with liver damage of the present invention are not particularly limited and ES cells and blastocysts from various mouse lines can be used. For example, cells from 129SvEv mice, C57BL/6J mice, or the like can be used.

According to the method for preparing the mouse with liver damage of the present invention, the resulting mouse can have a transgene in a heterozygous form. Therefore, the transgenic mice can be efficiently prepared in large numbers, and desired transgenic mice can be selected and prepared efficiently from the thus obtained transgenic mice by screening for mice having a high degree of liver damage while having the uPA gene in a heterozygous form.

Moreover, the mouse with liver damage of the present invention has mouse productivity higher than that of conventional transgenic mice having the uPA gene in a homozygous form, since the mouse with liver damage of the present invention can have the uPA gene in a heterozygous form. Specifically, first, many heterozygous female mice should be produced in order to obtain many homozygous mice. Thereafter, homozygous mice should be obtained by external fertilization or natural mating of the heterozygous mice. This process requires two generations and at least 6 months in total. Moreover, the thus obtained homozygous mice accounting for only about 25% of the total number of the thus obtained mice are obtained. In contrast, many heterozygous mice can be obtained in the second generation (via single generation) by performing external fertilization or natural mating with wild-type mice that can be purchased in large numbers from breeders. The time period required for this process is at least 3 months. Moreover, about 50% of the total number of mice obtained herein are heterozygous mice, indicating that a large number of necessary mice can be produced within a short time period highly efficiently. Also, when a cross-bred line produced with another genetically mutated mouse (e.g., gene deficiency or introduced genes) is used for an experiment, mice that can be efficiently used for the experiment can be obtained if heterozygous uPA transgenic mice can be used. For example, when mice each having the introduced uPA gene in a heterozygous form and another type of gene mutation in a heterozygous form are used with each other to produce a mouse having the uPA gene and another type of gene mutation in a double homozygous form, the thus obtained mice having both genes in a homozygous form account for only 6% of the thus obtained mice. Furthermore, female and male homozygous mice should be obtained and then breeding and production should be performed in order to obtain a considerable number of mice to be used for an experiment. Meanwhile, the thus obtained mice having the uPA gene in a heterozygous form and another type of gene mutation in a homozygous form account for about 12.5%. This indicates that mice required for an experiment can be obtained at this time point with production efficiency higher than that of the production of mice having both genes in a homozygous form. This means that a considerable number of mice that can be used for an experiment can be obtained earlier by a single generation than the production of mice having both genes in a homozygous form. As described above, the fact that heterozygous mice can be used enables to obtain high production efficiency, so as to contribute to save the space for an animal room to be used for keeping and obtaining mice necessary for the experiment, resulting in a shorter period required for production, a drastic reduction in the number of mice to be used, and the reduction of experimenters' efforts.

In the present invention, examples of the "mouse with liver damage" include portions of the mouse. The term "a portion(s) of the mouse" refers to, mouse-derived tissues, body fluids, cells, and disrupted products thereof or extracts therefrom, for example (the examples thereof are not particularly limited to them). Examples of such tissues include, but are not particularly limited to, heart, lungs, kidney, liver, gallbladder, pancreas, spleen, intestine, muscle, blood vessel, brain, testis, ovary, uterus, placenta, marrow, thyroid gland, thymus gland, and mammary gland. Examples of body fluids include, but are not particularly limited to, blood, lymph fluids, and urine. The term "cells" refers to cells contained in the above tissues or body fluids, and examples thereof include cultured cells, sperm cells, ova, and fertilized eggs obtained by isolation or culture thereof. Examples of cultured cells include both primary cultured cells and cells of an established cell line. Examples of the portions of the mouse also include tissues, body fluids, and cells at the developmental stage (embryonic stage), as well as the disrupted products or extracts thereof. In addition, an established cell line from the mouse with liver damage of the present invention can be established using a known method (Primary Culture Methods for Embryonic Cells (*Shin Seikagaku Jikken Koza* (New Biochemical Experimental Lecture Series), Vol. 18, pages 125-129, TOKYO KAGAKU DOZIN CO., LTD., and Manuals for Mouse Embryo Manipulation, pages 262-264, Kindai Shuppan)).

The present invention further provides an immunodeficient mouse with liver damage. The immunodeficient mouse with liver damage of the present invention can be used as a host mouse for transplantation of human hepatocytes. The immunodeficient mouse with liver damage of the present invention can be obtained by crossing the above mouse with liver damage with an immunodeficient mouse.

Examples of the "immunodeficient mouse" may be any mouse that does not exhibit rejection against hepatocytes (in particular, human hepatocytes) from a different animal origin, and include, but are not limited to, SCID (severe combined immunodeficiency) mice exhibiting deficiency in T- and B-cell lines, mice (NUDE mice) that have lost T cell functions because of genetic deletion of the thymus gland, and mice (RAG2 knockout mice) produced by knocking out the RAG2 gene by a known gene targeting method (Science, 244: 1288-1292, 1989). A preferable example thereof is a SCID mouse.

The immunodeficient mouse with liver damage of the present invention has a gene that specifies the phenotype of immunodeficiency in a homozygous form. The immunodeficient mouse with liver damage of the present invention may also have a DNA fragment containing the uPA gene from the above mouse with liver damage in either a heterozygous form or a homozygous form. Even when the immunodeficient mouse with liver damage of the present invention has the uPA gene in a heterozygous form, human hepatocytes transplanted into the mouse can engraft for long periods of time. Examples of the genotype of the immunodeficient mouse with liver damage of the present invention include, but are not limited to, uPA (+/−)/SCID (+/+) and uPA (+/+)/SCID (+1+).

Heterozygous mice or homozygous mice can be selected by screening, as described above, chromosomal DNAs separated and extracted from the tails of the thus obtained offspring by Southern hybridization or a PCR method.

In the present invention, examples of the "immunodeficient mouse with liver damage" include portions of the mouse. The term "a portion of the mouse" is as defined above.

Moreover, the present invention provides a chimeric mouse having human hepatocytes. The chimeric mouse of the present invention is immunologically deficient, which is prepared by introducing, in a heterozygous form, a DNA fragment containing cDNA that encodes an urokinase-type plasminogen activator operably linked under the control of the liver-specific promoter and enhancer region, and has a chimeric liver containing human hepatocytes.

The chimeric mouse of the present invention can be prepared by transplanting human hepatocytes into the above immunodeficient mouse with liver damage of the present invention.

As human hepatocytes to be used for transplantation, human hepatocytes isolated from normal human liver tissue by a conventional method such as a collagenase perfusion method can be used. The thus separated hepatocytes can also be used by thawing after cryopreservation. Alternatively, the chimeric mouse hepatocytes, which are defined as the human hepatocytes separated by a technique such as a collagenase perfusion method from a chimeric mouse liver, in which mouse hepatocytes have been replaced by human hepatocytes, can be used in a fresh state, and the cryopreserved chimeric mouse hepatocytes are also available after thawing.

Such human hepatocytes can be transplanted into the liver via the spleen of the above immunodeficient mouse with liver damage. Such human hepatocytes can also be directly transplanted via the portal vein. The number of human hepatocytes to be transplanted may range from about 1 to 2,000,000 cells and preferably range from about 200,000 to 1,000,000 cells. The gender of the immunodeficient mouse with liver damage is not particularly limited. Also, the age on days of the immunodeficient mouse with liver damage upon transplantation is not particularly limited. When human hepatocytes are transplanted into a young mouse (early weeks of age), human hepatocytes can more actively proliferate as the mouse grows. Hence, about 0- to 40-day-old mice after birth, and particularly about 8- to 40-day-old mice after birth are preferably used.

Mice after transplantation can be maintained by a conventional method. After transplantation, blood is collected periodically from the mouse tail, and then the human albumin concentration in mouse blood is measured. Since human albumin concentration correlates with the replacement rate of human hepatocytes in the mouse liver, the degrees of the engraftment and the proliferation of human hepatocytes can be inferred with the value of human albumin concentration. A mouse inferred to have a replacement rate of 70% or more on the basis of the blood human albumin concentration can be used as a chimeric mouse with a high degree of replacement for pharmacokinetic studies, infection studies with hepatitis virus, or the like. In the case of mice, when about 1 to $10 \times 10^5$ human hepatocytes are transplanted, the mouse is maintained for about 40 to 100 days, and thus a blood human albumin concentration ranging from 100,000 to 30,000,000 ng/mL can be obtained.

The thus transplanted human hepatocytes account for at least 10%, 20% or more, 30% or more, 40% or more, 50% or more, 60% or more, 70% or more, 80% or more, 90% or more, 95% or more, or even a higher percentage of hepatocytes in the liver of the chimeric mouse.

Transplanted human hepatocytes retain the functions and the properties of normal human hepatocytes in the liver of the chimeric mouse for at least 2 weeks, 3 or more weeks, 4 or more weeks, 5 or more weeks, 10 weeks, 20 weeks, 30 weeks, and 40 weeks, and most preferably for a period during which the mouse survives.

Examples of "the functions and the properties of human hepatocytes" include, but are not limited to, drug-metabolizing functions, protein synthesis, gluconeogenesis, urea synthesis, bile synthesis, lipid synthesis, glucose metabolism, detoxication, and infectiveness against hepatitis virus.

Transplanted human hepatocytes retain 50% or more, 60% or more, 70% or more, 80% or more, 90% or more, 95% or more, or even a higher percentage of the functions and the properties in the normal human liver.

The present invention further provides a method for screening for a substance that affects human liver functions, with the use of the above chimeric mouse.

An example of the method is an evaluation method comprising the following steps of:
(a) administering a test substance to the above chimeric mouse;
(b) measuring one or more values selected from the group consisting of the human albumin concentration, the body weight curve, the liver-weight-to-body-weight ratio, the total albumin level, the total protein level, the ALT level, the AST level, and the total bilirubin level in the chimeric mouse to which the test substance is administered in (a); and
(c) selecting a test substance that causes an increase or an decrease in any one or more of the human albumin concentration, the body weight curve, the liver-weight-to-body-weight ratio, the total albumin level, the total protein level, the ALT level, the AST level, and the total bilirubin level measured in (b), compared with the human albumin concentration, the body weight curve, the liver-weight-to-body-weight ratio, the total albumin level, the total protein level, the ALT level, the AST level, and the total bilirubin level of the chimeric mouse to which no test substance is administered.

Examples of the "test substance" in the method of the present invention are not particularly limited and include natural compounds, organic compounds, inorganic compounds, proteins, antibodies, peptides, and single compounds such as an amino acid, and nucleic acids, as well as compound libraries, expression products from gene libraries, cell extracts, cell culture supernatants, products of fermenting microorganisms, extracts from marine creatures, plant extracts, extracts from prokaryotic cells, extracts from eukaryotic single cells, and extracts from animal cells. These products may be purified products or crude products such as plant, animal, or microbial extracts. Also, a method for producing a test substance is not particularly limited. A test substance to be used herein may be a substance isolated from a natural product, synthesized chemically or biochemically, or prepared by genetic engineering techniques.

The above test substance can be adequately labeled and then used as necessary. Examples of labels include radiolabels and fluorescent labels. Examples of the test substance include, in addition to the above test samples, mixtures of a plurality of types of these test samples.

In this method, examples of a method for administering a test substance to mice are not particularly limited. Such an administration method can be adequately selected from among oral administration or parenteral administration such as subcutaneous, intravenous, local, transdermal, and enteral (intrarectal) administration, depending on the type of a test substance to be administered.

The rate of replacement by human hepatocytes in the mouse liver can be predicted by measuring the human albumin concentration in mouse blood by ELISA, immunonephelometry, or the like. For prediction, a correlation curve of human albumin concentrations and replacement rates should be prepared in advance as described below. Blood is collected before the autopsy of a chimeric mouse, and then the human albumin concentration is determined. Frozen sections or paraffin sections are prepared from the entire liver or partial hepatic loves collected upon autopsy. Immunostaining is performed using an antibody specific to human hepatocytes, such as a human specific cytokeratin 8/18 (hCK8/18) antibody. Photographs of the sections are taken under a microscope, the proportion of the hCK8/18-positive area per liver section is calculated to give a replacement rate. Human albumin concentrations and replacement rates are plotted on a graph, thereby finding a correlation equation. The human albumin concentration in mouse blood is entered to the correlation equation, so that a replacement rate can be roughly calculated. Furthermore, the body weight is measured over time, the health status of the mouse can be predicted. A biochemical test is performed for blood collected upon autopsy. For example, a total albumin level, a total protein level, and the like are measured, and thus the health status of the mouse can be clarified. The degree of liver damage of a chimeric mouse can be clarified by measuring the liver weight, the body weight, ALT, AST, and the total bilirubin levels, for example. Specifically, the effects of a test substance against human hepatocytes can be determined using increases or decreases in these numerical figures as indicators.

The present invention further provides a method for evaluating hepatotoxicity of a test substance against human hepatocytes, with the use of the above chimeric mouse.

An example of this method is an evaluation method comprising the following steps of:
(a) administering a test substance to the above chimeric mouse;
(b) measuring one or more values selected from the group consisting of the human albumin concentration, the body weight curve, the liver-weight-to-body-weight ratio, the total albumin level, the total protein level, the ALT level, the AST level, and the total bilirubin level in the chimeric mouse to which the test substance is administered in (a); and
(c) evaluating the effect of the test substance on human hepatocytes using, as an indicator, an increase or a decrease in any one or more of the human albumin concentration, the body weight curve, the liver-weight-to-body-weight ratio, the total albumin level, the total protein level, the ALT level, the AST level, and the total bilirubin level measured in (b), compared with the human albumin concentration, the body weight curve, the liver-weight-to-body-weight ratio, the total albumin level, the total protein level, the ALT level, the AST level, and the total bilirubin level of the chimeric mouse to which no test substance is administered.

Examples of the "test substance" and the "administration method" thereof include those defined above.

As described above, the degree of liver damage of a chimeric mouse can be analyzed on the basis of human albumin concentration, body weight curve, liver-weight-to-body-weight ratio, total albumin level, total protein level, ALT level, AST level, and total bilirubin level. With the use of increases or decreases in these numerical figures as indicators, the toxicity of the test substance against human hepatocytes can be determined and evaluated.

The present invention further provides a method for screening for a substance effective for treatment of viral hepatitis, with the use of the above chimeric mouse.

An example of this method is an evaluation method comprising the following steps of:
(a) inoculating a hepatitis virus into the above chimeric mouse;
(b) administering a test substance to the chimeric mouse inoculated with the hepatitis virus in (a);
(c) measuring one or more values selected from the group consisting of the human albumin concentration, the body weight curve, the liver-weight-to-body-weight ratio, the total albumin level, the total protein level, the ALT level, the AST level, the total bilirubin level, the viral load, and the amount of a virus-derived protein of the chimeric mouse to which the test substance is administered in (b); and
(d) selecting a test substance causing a change in any one or more of the human albumin concentration, the body weight curve, the liver-weight-to-body-weight ratio, the total albumin level, the total protein level, the ALT level, the AST level, the total bilirubin level, the viral load, and the amount of a virus-derived protein measured in (c), compared with the human albumin concentration, the body weight curve, the liver-weight-to-body-weight ratio, the total albumin level, the total protein level, the ALT level, the AST level, the total bilirubin level, the viral load, and the amount of a virus-derived protein in the chimeric mouse to which no test substance is administered.

Examples of hepatitis viruses to be used for inoculation include hepatitis type A virus, hepatitis type B virus, hepatitis type C virus, hepatitis type D virus, and hepatitis type E virus. Viruses can be inoculated via intravascular or intraperitoneal administration.

The above chimeric mouse to be used in this method is preferably a mouse that satisfies at least one of the following conditions: 3 or more weeks have passed after the transplantation of human hepatocytes; the blood human albumin concentration is 1 mg/mL or higher; and human hepatocytes account for 10% or more of all hepatocytes.

Examples of the "test substance" and the "administration method" thereof include those defined above.

The degree of liver damage due to hepatitis viruses can be found on the basis of human albumin concentration, body weight curve, liver-weight-to-body-weight ratio, total albumin level, total protein level, ALT level, AST level, total bilirubin level, viral load, and the amount of a virus-derived protein. With the use of changes in these numerical figures as indicators, the effectiveness of a test substance in treatment of viral hepatitis can be determined and evaluated.

All publications, patents, and patent applications cited herein are incorporated herein by reference in their entirety.

Hereafter, the present invention is described in greater detail with reference to the following examples.

Example 1. Preparation of uPa Transgenic Mice Using DNA Microinjection Method (1) Preparation of Vector Containing an uPA Gene and an Albumin Promoter Regarding a uPA gene, total RNA was extracted from mouse liver by an AGPC method (acid-guanidinium-isothiocyanate-phenol-chloroform), and then dissolved in RNase-free water. A reverse transcription reaction was performed using the above-obtained total RNA, a uPA gene-specific primer (the antisense sequence having a length from the $1341^{st}$ to the $1360^{th}$ nucleotides) prepared based on the sequence of the uPA gene (Accession No.: NM008873 (SEQ ID NO: 11)) registered in the published database, and Long Range Reverse Transcriptase (Qiagen) at 25° C. for 10 minutes, and then performed at 42° C. for 90 minutes. After 5 minutes of reverse transcriptase inactivation treatment at 85° C., RNaseH (Invitrogen) was added, the resultant was treated at 37° C. for 20 minutes to digest mRNA, and thus only cDNA remained. PCR was performed using the thus synthesized cDNA as a template. The above reaction solution in an amount 1/10 the total amount thereof was added. As an enzyme, Phusion DNA polymerase (Fynnzymes) was used. A PCR primer (the sense sequence having a length from the $39^{th}$ nucleotide to the $61^{st}$ nucleotide) was prepared based on the sequence of the uPA gene (Accession No.: NM008873). The fragment amplified by PCR has a length of nucleotide Nos. 39-1360. The thus obtained DNA fragment was introduced into an expression plasmid having a mouse albumin promoter/enhancer described later, thereby constructing "mAlb uPAInt2." The configuration of the "mAlb uPAInt2" gene is shown in FIG. 1. The 2nd exon, intron, and the 3rd exon of rabbit β globin, the ORF portion of mouse uPA, and polyA signal in the 3rd exon of rabbit β globin were ligated downstream of the mouse albumin enhancer/promoter.

(2) Microinjection of DNA into the Pronuclei of Fertilized Eggs

The concentration of the DNA fragment was adjusted to 3 ng/4, and then the DNA fragment was injected into pronuclear stage fertilized eggs collected from CB-17/Icr and Scid-beige cross-bred mice. DNA was injected into such a fertilized egg by microinjection. 635 out of 748 fertilized eggs, into which DNA had been injected, survived, and 469 eggs thereof differentiated into the 2-cell stage embryos. The 2-cell stage embryos were transplanted into the uterine tubes of recipient ICR mice treated in advance to be in pseudopregnancy. 108 offspring were obtained. Whether or not the thus obtained offspring contained the uPA gene was analyzed by PCR (The Tokyo Metropolitan Institute of Medical Science). As a result of PCR, it was confirmed that one mouse contained the target DNA. A uPA transgenic mouse line was established from the one mouse.

(3) Measurement and Analysis of Serum ALT Levels in uPA Transgenic Mice

Blood was collected from the thus obtained mice having the uPA gene, so as to obtain the serum. Subsequently, the effect due to the expression of the uPA gene in the liver, and specifically, the damage of hepatocytes were analyzed by measuring the ALT levels. The ALT levels were measured using "Transaminase CII-Test Wako" (Wako Pure Chemical Industries, Ltd., cat #431-30901). After serum collection, serum samples were preserved at −80° C. until measured.

The method for measuring ALT was performed on 1/20 the scale of the standard procedure 1 included with "Transaminase CII-Test Wako". First, a substrate enzyme solution for ALT: 10 mL of a substrate buffer for ALT was added to 1 vial of an enzyme agent for ALT and the enzyme agent was dissolved in the buffer. Furthermore, a chromogenic solution: 40 mL of a color former solution was added to 1 vial of color former and the color former was dissolved in the solution.

Next, a CORNING 25850 96-well U-bottomed plate was prepared on ice. A serum sample (1 μL) was added to the plate. The plate was removed from ice, 25 μL of the substrate enzyme solution was added, and then heated at 37° C. for 5 minutes. STND (×1/2 dilution: 1 μL, ×1:1, 2 μL) was added to empty wells, and then 25 μL of the chromogenic solution was added to each well. The substrate enzyme solution (25 μL) was added to wells containing STND, and then heated at 37° C. for 20 minutes. A stop solution (100 µl) was added to each well. The solution was stirred well with a plate mixer, and then absorbance was measured at 570 nm within 60 minutes after stirring. A calibration curve was prepared using the measurement value of STND, thereby calculating the values representing the activity in samples.

No mouse with a high ALT level was confirmed from among mice subjected to measurement. The uPA transgenic mouse of interest must exhibit a condition wherein the expression level of the uPA gene is optimum for the subsequent hepatocyte transplantation. Mice exhibiting such optimum expression level should be selected after preparation of many uPA transgenic mice. It was revealed that this method is not a suitable for a method for probabilistically preparing such optimum mice in this case, because of the limited efficiency of the preparation of transgenic mice.

Example 2. Preparation of uPa Transgenic Mice
Via ES Cells (1) Establishment of ES Cells Prepared by Inserting the uPA Gene In this example, a uPA gene insertion vector "mAlb uPAInt2ES" (FIG. 2) was constructed and used. This vector was constructed by introducing a neomycin resistance gene that is expressed under the control of an SV40 promoter to the "mAlb uPAInt2" plasmid in order to impart drug selectivity in ES cells. The vector was introduced by electroporation into ES cells obtained from a 129SvEv mouse, followed by selective culture using G418. The thus obtained G418-resistant colonies were subjected to the testing by PCR for ES cells into which the gene had been introduced. This is as described specifically below.

A uPA gene insertion vector (uPA) DNA (25-30 µg) was linearized by cleavage with a restriction enzyme, and then purified. The DNA was suspended in an electroporation buffer (20 mM HEPES pH7.0, 137 mM NaCl, 5 mM KCl, 6 mM D-glucose, 0.7 mM $Na_2HPO_4$) containing $3 \times 10^6$ mouse ES cells. Gene transfer was performed under the conditions of Field Strength 185V/cm and Capacitance 500 Selective culture was performed with G418 (Geniticin) (SIGMA, G-9516) with a final concentration of 200 µg/mL, 24 hours after gene transfer. ES cells were cultured using a Dulbecco's modified Eagle's medium (DMEM) (Gibco/BRL, 11965-084) culture solution supplemented with fetal bovine serum having a final concentration of 15% (Hyclone, SH30071), L-glutamine having a final concentration of 2 mM (Gibco/BRL, 25030-081), non-essential amino acids each having a final concentration of 100 µM (Gibco/BRL, 11140-050), HEPES having a final concentration of 10 mM (Gibco/BRL, 15630-080), penicillin/streptomycin each having a final concentration of 100 U/mL (Gibco/BRL, 15140-122), β-mercaptoethanol having a final concentration of 100 µM (SIGMA, M-7522), and ESGRO (LIF) having a final concentration of 1000 U/mL (Gibco/BRL, 13275-029) (hereinafter referred to as "ES medium").

Moreover, as feeder cells for ES cells, MEF (Mouse Embryonic Fibroblast) cells isolated from E14.5 embryos were used. A culture solution used herein was a DMEM (Gibco/BRL, 11965-084) culture solution supplemented with fetal bovine serum having a final concentration of 10% (Hyclone, SH30071), L-glutamine having a final concentration of 2 mM (Gibco/BRL, 25030-081), non-essential amino acids each having a final concentration of 100 µM (Gibco/BRL, 11140-050), and penicillin/streptomycin each having a final concentration of 100 U/mL (Gibco/BRL, 15140-122) (hereinafter, referred to as "MEF medium"). MEF cells cultured to confluency in a 150-$cm^2$ flask were removed with trypsin/EDTA (0.05%/1 mM, Gibco/BRL, 25300-047) and then plated again on four 10 cm dishes, two 24-well plates, two 6-well plates, six 25 $cm^2$-flasks, and two 75 $cm^2$ flasks at optimal concentrations.

(2) Adjustment of ES Cells for Genotype Analysis

On day 5 after gene transfer, G418-resistant colonies that had appeared were passaged to a 24-well plate, as described below. Specifically, G418-resistant colonies were transferred to a 96-well microplate containing 150 µL of a trypsin/EDTA solution using Pipetman (Gilson). After 20 minutes of treatment within an incubator at 37° C., pipetting was performed with Pipetman to obtain single cells. The cell suspension was transferred to a 24-well plate and then culture was continued. Two days later, cells on the 24-well plate were divided into two groups, cells for cryopreservation and cells for DNA extraction. Specifically, 500 µL of trypsin/EDTA was added to cells, cells were treated for 20 minutes within an incubator at 37° C., and then 500 µL of ES medium was added. Gentle pipetting was performed with Pipetman, so as to obtain single cells. Subsequently, a half of the cell suspension was transferred to a 24-well plate containing 1 mL of ES medium. One mL of ES medium was also added to the original 24-well plate. Two days later, the medium in one of the 24-well plates was removed. 1 mL of medium for freezing prepared by adding fetal bovine serum having a final concentration of 10% and dimethyl sulfoxide (DMSO) having a final concentration of 10% (Sigma, D-5879) to an ES medium was added. The resultant was sealed and then cryopreserved at −70° C.

ES cells into which the gene had been introduced were tested by PCR as described below. Specifically, medium was removed from each well of the 24-well plates in which cells had grown to confluency. After washing with PBS, 250 µL of a dissolution buffer (1% SDS, 20 mM EDTA, 20 mM Tris pH7.5) and 5 µL of proteinase K (20 mg/mL) were added and then the resultant was shaken well, followed by heating at 52° C. for dissolution. DNA was extracted from a dissolved sample by phenol/chloroform extraction, and then the resultant was used as template DNA for PCR.

(3) Method for analyzing the genotype of ES cells: ES cells into which the uPA gene had been introduced were selected by the following procedure.

PCR primers used herein were set in rabbit β globin. The sequences are: a sense primer: GGGCGGCGGTACC-GATCCTGAGAACTTCAGGGTGAG (SEQ ID NO: 1) and an antisense primer: GGGCGGCGGTACCAATTCTTTGC-CAAAATGATGAGA (SEQ ID NO: 2). Reaction was performed according to the method included with AmpiTaq-Gold (ABI). After 9 minutes of activation of the enzyme at 95° C., the cycle of PCR [94° C. for 30 seconds (denaturation), 63° C. for 30 seconds (annealing), and 72° C. for 1 minute (extension)] was repeated 40 times. After the completion of the reaction, the reaction solution was subjected to 2% agarose gel electrophoresis, so as to confirm PCR products.

Clones for which gene transfer had been confirmed by PCR analysis were thawed by heating the previously cryopreserved 96-well plate to 37° C., and then passaged to a 24-well plate. Clones in the 24-well plate were cultured for 24 hours at 37° C., medium exchange was performed to remove DMSO and liquid paraffin. When each clone reached 75% to 90% confluency, respectively, clones were passaged from the 24-well plate to a 6-well plate. Moreover, when clones that had grown to 75% to 90% confluency were obtained in 2 wells of the 6-well plate, clones in one well were cryopreserved and clones in the other well were used for injection into blastocysts and DNA extraction.

Cryopreservation was performed as follows. Specifically, cells were rinsed twice with PBS, 0.5 mL of Trypsin was added, and then the temperature was kept at 37° C. for 15 to 20 minutes to perform trypsin treatment. Furthermore, 0.5 mL of ES cell medium was added, pipetting was performed 35 to 40 times, and thus the mass of ES cells was completely dissociated. The cell suspension was transferred to a 15 mL centrifugal tube. Wells were further washed with 1 mL of ES cell medium, and then the resultants were collected in a tube. The tube was centrifuged at 1,000 rpm for 7 minutes. The medium was removed and then suspended again in 0.25 mL of ES cell medium. 0.25 mL of 2× frozen medium was added. The contents of the wells were transferred to a cryogenic vial, frozen at −80° C., and then preserved in liquid nitrogen.

Regarding cells for injection into blastocysts and DNA extraction, the mass of ES cells was completely dissociated, one-quarter thereof was used for injection into blastocysts, one-third of the remaining cells and two-third of the same were each passaged into a 60 mm dish coated with gelatin. When the former cells grew to confluency, genomic DNA for PCR analysis was extracted. When the latter cells grew to confluency, the cells were divided into three groups and then frozen.

(4) Preparation of Chimeric Mice Using ES Cells Having the uPA Gene

Regarding ES cell clones for which gene transfer had been confirmed, chimeric embryos were prepared using the blastocysts of C57BL/6J mice as host embryos. The chimeric embryos were each transplanted into the uterine horn of a pseudopregnant mouse to obtain offspring. Host embryos were collected by perfusion of the uterine tube and the uterus with Whitten's medium supplemented with 100 μM trypsin/EDTA on day 3 of pregnancy. 8-cell-stage embryos or morulae were cultured for 24 hours in Whitten's medium. The thus obtained blastocysts were used for injection. ES cells used for injection were dispersed by TE treatment on day 2 or 3 of passage, and then left to stand at 4° C. until the micromanipulation of these cells. As a pipette for injection of ES cells, glass capillary tubing (Sutter, inner diameter of about 20 μm) was used. A pipette for holding embryos used herein was processed as follows. A glass microtubule with an outer diameter of 1 mm (NARISHIGE) was pulled thin using a micropipette puller (Sutter, P-97/IVF), and then its tip with an outer diameter ranging from 50 μm to 100 μm was cut using a microforge (De Fonburun), and then processed to have an aperture of 10 μm to 20 μm. The pipette for injection and the pipette for holding were connected to a micromanipulator (Lica) with a piezo system (Primetech PAMS-CT150) connected thereto. As a chamber used for micromanipulation, perforated slide glass to which cover glass had been adhered with bees wax was used. Two drops of Hepes-buffered Whitten's medium supplemented with about 10 μL of 0.3% BSA were placed thereon, and then the top face was covered with mineral oil (Sigma). One drop contained about 100 ES cells, and the other drop contained about 20 expanded blastocysts. About 15 ES cells were injected per embryo. Micromanipulation was always performed under an inverted microscope. Manipulated embryos were transplanted into the uterine horns of recipient ICR female mice on day 2 of pseudo pregnancy. Recipient female mice that had not delivered offspring even on the predicted delivery date were subjected to cesarean section. The resulting offspring were raised by surrogate parents. As a result of injection of 45 clones of ES cells into the blastocysts of C57BL/6J mice, male chimeric mice were obtained from 39 clones.

(5) Test of the Transmission of the uPA Gene to the Germ Line

Chimeric mice were crossed with C57BL/6J mice, and then whether or not ES-cell-derived offspring were obtained was tested. If the germ cells of the chimeric mice were derived from ES cells, the thus delivered offspring would have wild-type hair color. If the germ cells of the chimeric mice were derived from the blastocysts of C57BL/6J mice, the thus delivered offspring would have black hair color. As a result of crossing, offspring having wild-type hair color were delivered in 25 lines, and thus the transmission of ES cells to the germ line was confirmed.

Next, DNA was extracted from the tail portions of these mice having wild-type hair color and then subjected to PCR to examine if the uPA gene had been transmitted. As a result, the transmission of the uPA gene was confirmed for ES-cell-derived offspring of 14 lines.

(6) Measurement and Analysis of Serum ALT Levels in uPA Transgenic Mice

Blood was collected from the thus obtained mice having the uPA gene, so as to obtain the serum. Subsequently, the effect due to the expression of the uPA gene in the liver, and specifically, the damage of hepatocytes were analyzed by measuring the ALT levels. The ALT levels were measured using "Transaminase CII-Test Wako" (Wako Pure Chemical Industries, Ltd., cat #431-30901). After serum collection, serum samples were preserved at −80° C. until measured.

The method for measuring ALT was performed on 1/20 the scale of the standard procedure 1 included with "Transaminase CII-Test Wako". First, a substrate enzyme solution for ALT: 10 mL of a substrate buffer for ALT was added to 1 vial of an enzyme agent for ALT and the enzyme agent was dissolved in the buffer. Furthermore, a chromogenic solution: 40 mL of a color former solution was added to 1 vial of color former and the color former was dissolved in the solution.

Next, a CORNING 25850 96-well U-bottomed plate was prepared on ice. A serum sample (1 μL) was added to the plate. The plate was removed from ice, 25 μL of the substrate enzyme solution was added, and then heated at 37° C. for 5 minutes. STND (×1/2 dilution: 1×1:1, 2 μL) was added to empty wells, and then 25 μL of the chromogenic solution was added to each well. The substrate enzyme solution (25 μL) was added to wells containing STND, and then heated at 37° C. for 20 minutes. A stop solution (100 μl) was added to each well. The solution was stirred well with a plate mixer, and then absorbance was measured at 570 nm within 60 minutes after stirring. A calibration curve was prepared using the measurement value of STND, thereby calculating the values representing the activity in samples.

Of 14 mouse lines measured, 3 lines of heterozygous mice were confirmed to have high ALT levels (FIG. 3).

The following experiment of human hepatocyte transplantation was performed using 2 lines (#1C2 and #2C7) of mice with high ALT levels from among the thus obtained 3 lines.

Example 3. Preparation of Chimeric Mice (1) Immunodeficient Mice with Liver Damage uPA-Tg mice (heterozygote, +/−) prepared in Example 2 above were back-crossed twice with SCID-bg mice, thereby obtaining mice having the genotype of uPA-Tg(+/−) SCID (+/+). Sperm cells were collected from the male mice, external fertilization was performed with unfertilized eggs of SCID mice (homozygote, +/+), and then the fertilized eggs were returned into surrogate mother mice. Among offspring delivered, mice having a Tg gene therein were selected and then subjected to natural mating, so that mice having both genotypes (uPA-Tg(+/−)/SCID (+/+)) were obtained. uPA-Tg (+/−) and uPA-Tg(−/−) were distinguished from each other by a genome PCR method using sequences specific to the transgene as primers.

```
Forward primer
                                     (SEQ ID NO: 3)
5'-GGGCGGCGGTACCGATCCTGAGAACTTCAGGGTGAG-3'

Reverse primer
                                     (SEQ ID NO: 4)
5'-GGGCGGCGGTACCAATTCTTTGCCAAAATGATGAGA-3'
```

In addition, SCID (+/+), SCID (+/−), and SCID(−/−) were distinguished from each other by a PCR-RFLP method.

Next, the thus obtained uPA-Tg(+/−)/SCID(+/+) mice were crossed each other, thereby obtaining uPA-Tg(+/+)/SCID(+/+) and uPA-Tg(+/−)/SCID(+/+). uPA-Tg(+/+) and uPA-Tg(+/−) were distinguished from each other by a Southern blotting method. About 5-mm tail portions were cut from 8- to 10-day-old mice, and then solubilized with a 3 SDS, proteinase K solution. Protein components mixed therein were removed by phenol and chloroform extraction. RNA mixed therein was denatured using DNAse-free RNase A, and then macromolecular genomic DNA was precipitated by isopropanol precipitation. The above genomic DNA was washed with 70% ethanol, air dried, and then dissolved again in TE. Genomic DNA extracted from a specimen, positive control genomic DNA, and negative control genomic DNA (5 μg each) were completely digested with EcoR1. The thus generated DNA fragments were separated by agarose electrophoresis, and then transferred to a nylon membrane. A DNA fragment appropriate as a probe for Southern hybridization was purified (379 bp) from uPA cDNA probe/TA using restriction enzyme EcoR1. The above DNA fragment was labeled with [32P] by a random prime method. The DNA fragment transferred to the nylon membrane was hybridized with the RI-labeled uPA cDNA probe. Non-specifically bound probes were removed by washing. Radioactive signals from the foreign gene introduced in mAlb-uPA-Int2 Tg mouse candidates were exposed to an X-ray film and thus detected. Wild-type-locus-derived 1.5-kb specific signals and mutant-locus-derived 0.4 kb (wt: 1.5 kb) specific signals were detected, thereby determining the genotype of individual mAlb-uPA-Int2 Tg mice.

(2) Transplantation of Human Hepatocytes

As human hepatocytes, hepatocytes (Lot No.BD85, boy, 5 years old) purchased from BD Gentest were used. The cryopreserved hepatocytes were thawed and used according to a conventionally known method (Chise Tateno et al, Near-completely humanized liver in mice shows human-type metabolic responses to drugs. Am J Pathol 165: 901-912, 2004).

2- to 4-week-old 7 #1C2 homozygous, 4 #1C2 heterozygous, 4 #2C7 homozygous, and 7 #2C7 heterozygous uPA-Tg/SCID mice were ether-anesthetized. An about 5-mm incision was made in a flank, and then 2.5×10$^5$ human hepatocytes were injected via the inferior splenic pole. The spleen was returned to the peritoneal cavity and then the site was sutured. One #1C2 homozygous mouse died on day 30 of transplantation.

Figure 4:
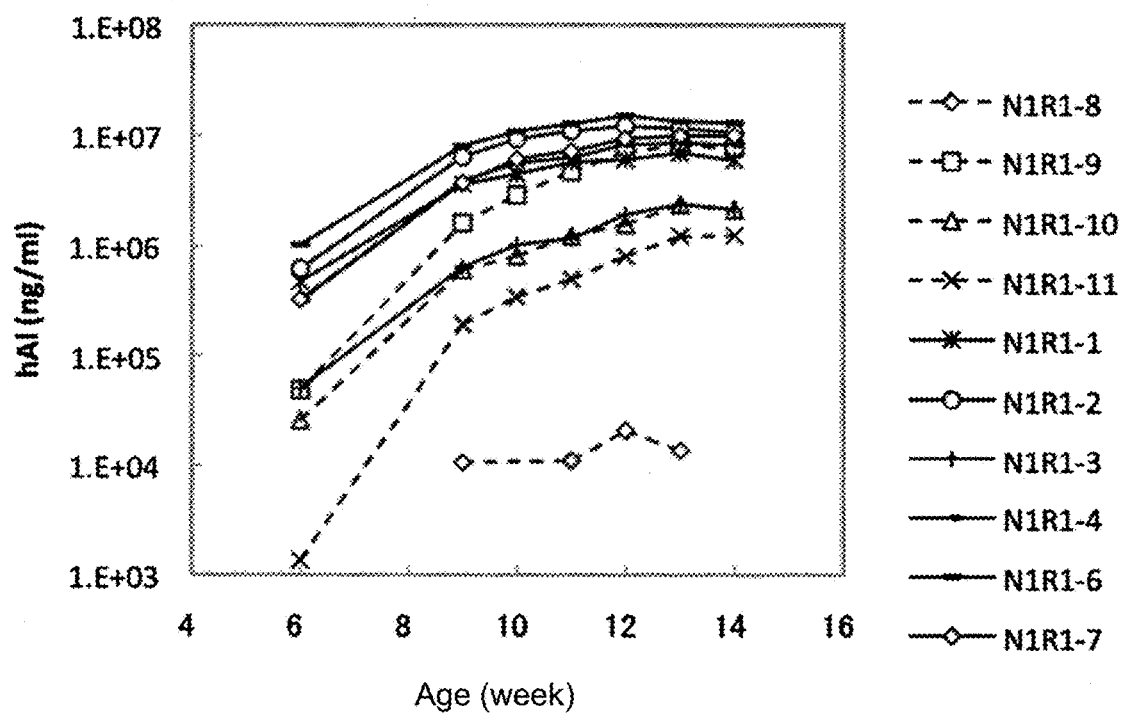
FIG. 4 shows the results of measuring human albumin concentrations in mouse blood (top) and body weights (bottom) of #1C2 mice (up to 14 weeks old) after transplantation of human hepatocytes into the mice. The solid lines denote homozygous mice and dotted lines denote heterozygous mice.
Figure 4:
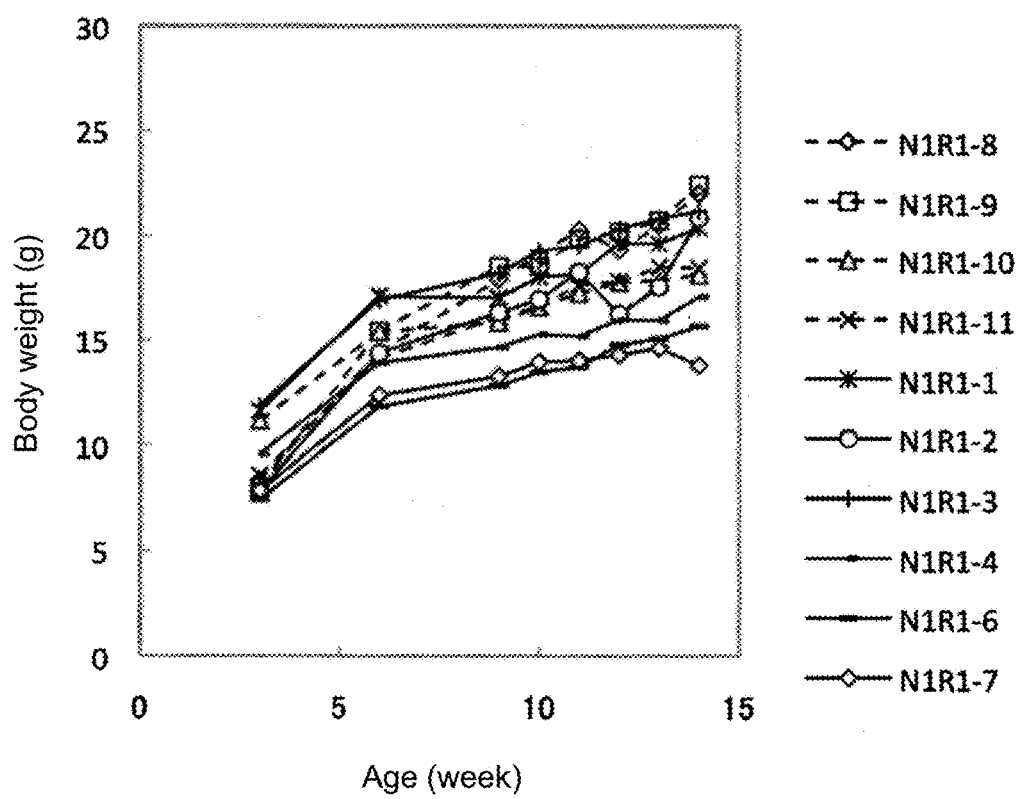
Figure 5:
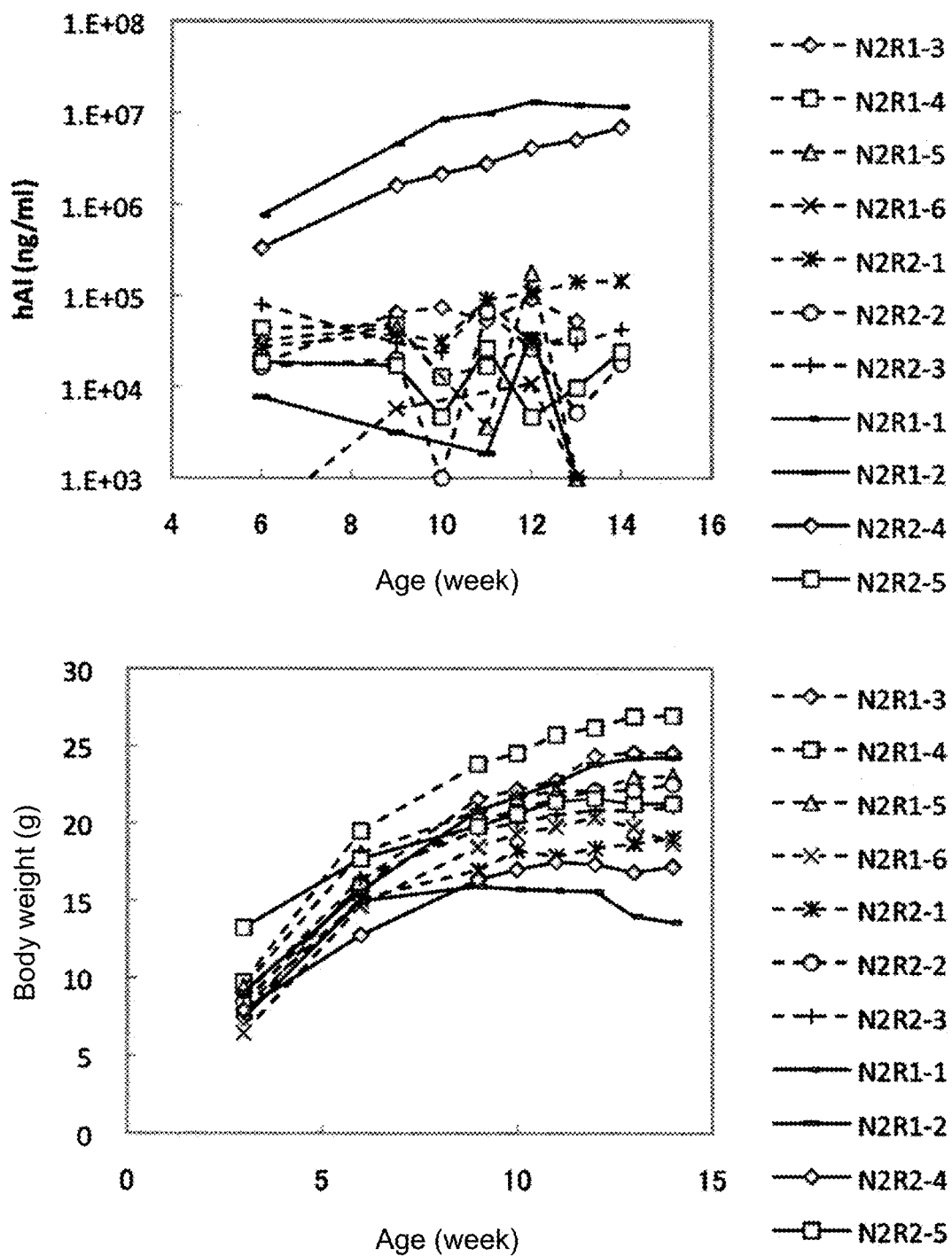
FIG. 5 shows the results of measuring human albumin concentrations in mouse blood (top) and body weights (bottom) of #2C7 mice (up to 14 weeks old) after transplantation of human hepatocytes into the mice. The solid lines denote homozygous mice and dotted lines denote heterozygous mice.

2 μL of blood was collected from mouse tail vein on weeks 3 and 6 after transplantation and then every week, and then added to 200 μL of LX-Buffer. Human albumin concentrations in mouse blood were measured by immunonephelometry using an autoanalyzer JEOL BM6050 (JEOL Ltd.). As a result, increases in human albumin concentration were observed for #1C2 homozygous, #1C2 heterozygous, and #2C7 homozygous mice. Specifically, mice with human albumin concentrations higher than 7 mg/mL were observed (FIG. 4 and FIG. 5). No increase in human albumin concentration was observed for #2C7 heterozygous mice (FIG. 5). A smooth gain in body weight was observed for all mice. The body weights of most #2C7 heterozygous mice were at high levels (FIG. 5).

Figure 6:
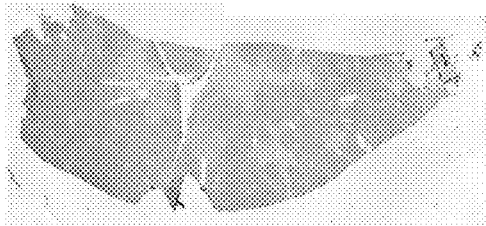
FIG. 6 shows the immunostaining images of chimeric mouse liver sections prepared using #1C2 homozygous, #1C2 heterozygous, and #2C7 homozygous mice immunostained with a human cytokeratin 8/18 antibody.
Figure 6:
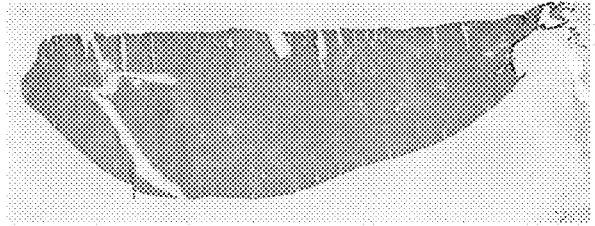
Figure 6:
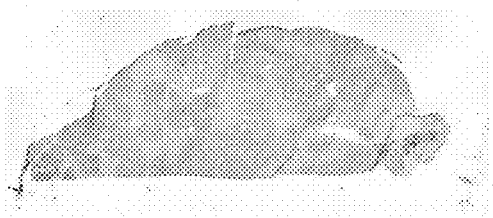
Figure 6:
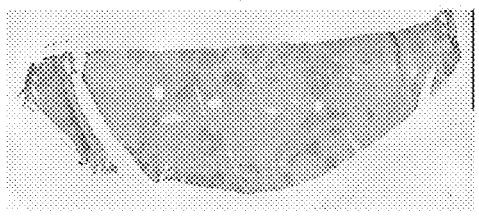
Figure 6:
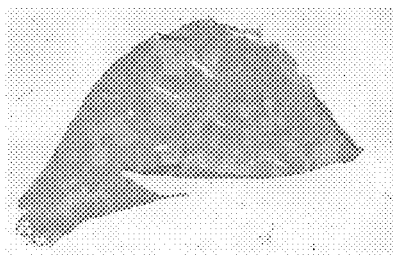
Figure 6:
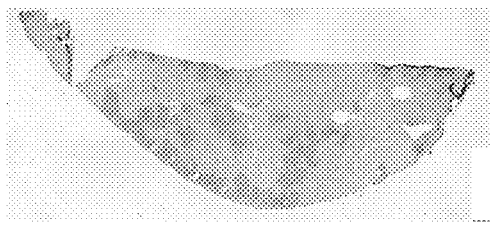
Figure 6:
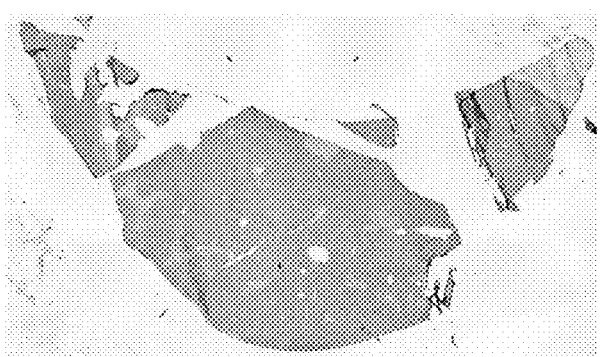
Figure 7:
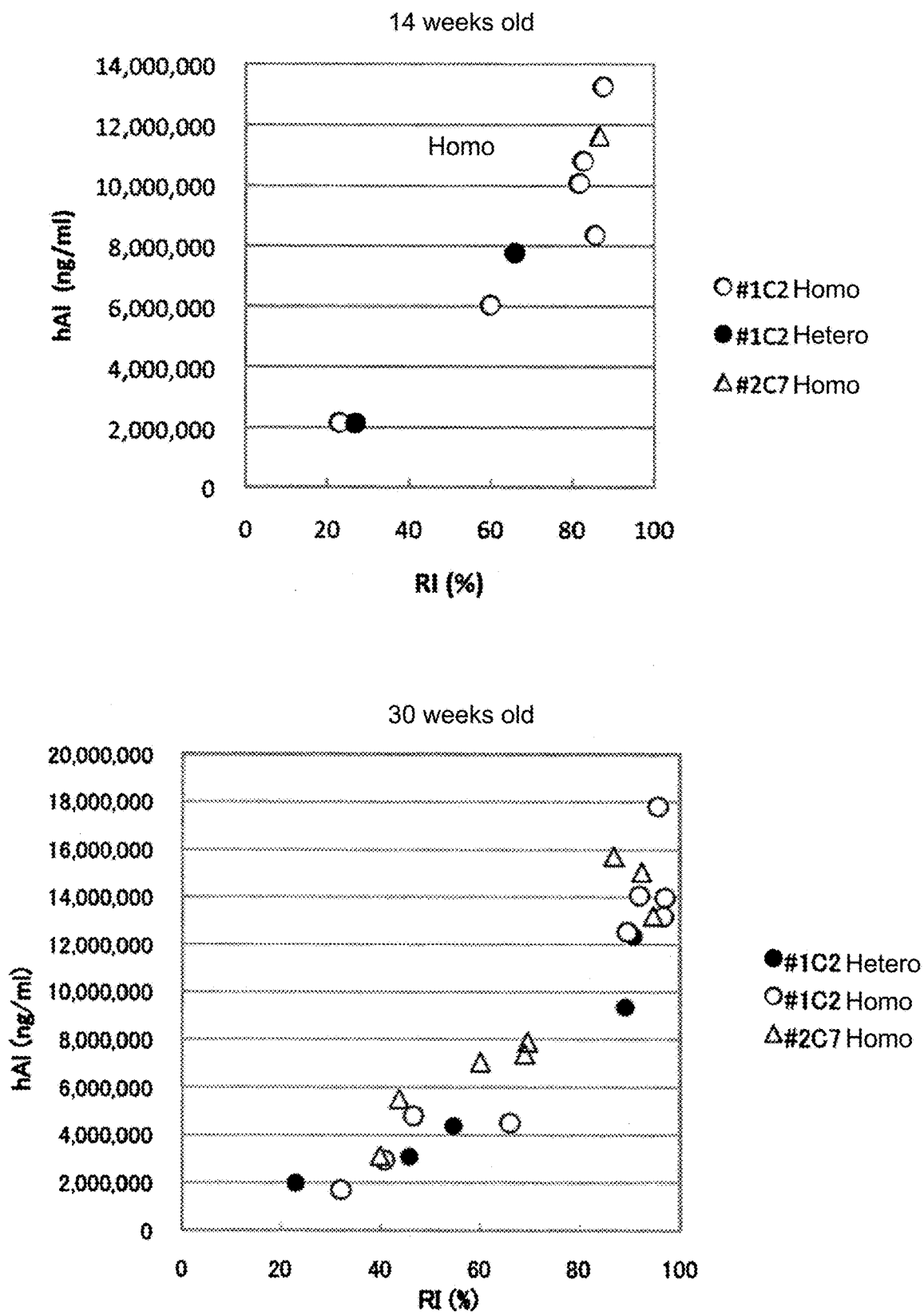
FIG. 7 shows the results of measuring the replacement rates in the livers of chimeric mice prepared using 14-week-old (top) and 30-week-old (bottom) #1C2 homozygous, #1C2 heterozygous, and 2C7 homozygous mice and human albumin concentrations in the mouse blood.

Chimeric mice (13- to 15-week-old) were anatomized 10 to 12 weeks after transplantation, and then liver and blood were collected. The frozen sections of 7 liver lobes were prepared, and then immunostaining was performed using a human-specific cytokeratin 8/18 (hCK8/18) antibody (FIG. 6). The hCK8/18 positive area per area of a frozen section was determined, thereby obtaining a replacement rate. As a result, #1C2 homozygous mice and #2C7 homozygous mice having a replacement rate of 70% or more were confirmed (FIG. 7). #1C2 heterozygous mice having a replacement rate of 60% or more were observed (FIG. 7). A correlation between human albumin concentrations in mouse blood and replacement rates was confirmed in a manner similar to those in conventionally known chimeric mice (Chise Tateno et al, described above) (FIG. 7). In terms of correlation, no clear difference was confirmed between #1C2 and #2C7, and, between heterozygous mice and homozygous mice (FIG. 7).

Human hepatocytes were transplanted into 2- to 4-week-old 28 #1C2 homozygous, 28 #1C2 heterozygous, 18 #2C7 homozygous, and 15 #2C7 heterozygous uPA-Tg/SCID mice. As a result, chimeric mice having high replacement rates, wherein the human albumin concentration in mouse blood was 7 mg/mL or higher, were #1C2 homozygous mice (61%), #1C2 heterozygous mice (36%), #2C7 homozygous mice (28%), and #2C7 heterozygous mice (0%) (FIG. 8-1, 2, FIG. 9-1, 2, FIG. 10, and FIG. 11).

Several 14- or 15-week-old mice (6 #1C2 homozygous mice, 6 #1C2 heterozygous mice, and 4 #2C7 homozygous mice) were inoculated with HBV or HCV (1×10$^4$ copies/mouse) via orbital venous plexus (FIG. 8-1, 2, 9-1, 2). On week 1 after inoculation, blood was collected via orbital venous plexus every week, HBV and HCV viral titers were determined by a real-time quantitative PCR method and a real-time quantitative RT-PCR method.

RNA was extracted from 5 μL of serum collected from each mouse inoculated with HCV using SepaGene RV-R (Sanko Junyaku Co., Ltd. (currently, EIDIA Co., Ltd.), Tokyo, Japan). RNA was dissolved in 10 μL of Nuclease-free water (Life Technologies Corporation, Carlsbad, Calif., USA) containing 1 mM DTT (Promega, Tokyo, Japan) and 0.4 U/μL ribonuclease inhibitor (Takara Bio Inc. Shiga, Japan). The thus dissolved RNA was preserved at −80° C. until the quantification of serum HCV RNA level.

TaqMan EZ RT-PCR Core Reagents (Life Technologies Corporation) and 2.5 μL of a dissolved undiluted RNA solution or diluted RNA solution were used for a PCR solution. PCR was performed under conditions of 50° C. for 2 minutes (Uracil-N-Glycosylase treatment)→60° C. for 30 minutes (reverse transcription reaction)→95° C. for 5 minutes (PCR initial activation)→[95° C. for 20 seconds (denaturation)→62° C. for 1 minute (annealing·extension reaction)]×50 cycles. Reaction and analyses were performed using ABI Prism 7500 (Life Technologies Corporation). Primers and a probe used herein are as follows.

Forward primer:
(SEQ ID NO: 5)
5'-CGGGAGAGCCATAGTGG-3'

Reverse primer:
(SEQ ID NO: 6)
5'-AGTACCACAAGGCCTTTCG-3'

Probe:
(SEQ ID NO: 7)
5'-CTGCGGAACCGGTGAGTACAC-3'
(5'-end: FAM, 3'-end: TAMRA)

As an HCV RNA standard, serum obtained from HCV-infected chimeric mice was used. The serum had been subjected to the determination of the HCV RNA level based on artificial HCV RNA, and preserved at −80° C. until the quantification of serum HCV RNA. When serum HCV RNA concentrations were measured, RNA was extracted from the serum, subjected to 10-fold serial dilution for use as the HCV RNA standard. The determination limit of the determination of serum HCV RNA using the HCV RNA standard ranges from $2.1 \times 10^4$ copies/mL to $2.1 \times 10^7$ copies/mL in serum.

DNA was extracted from 10 µL of serum collected from mice inoculated with HBV using SMI TEST EX-R&D (Code: R-35, Medical and Biological Laboratories Co., Ltd., Nagano, Japan). DNA was dissolved in 20 µL of Nuclease-free water. The thus dissolved DNA was preserved at −20° C. or lower until the quantification of HBV DNA.

5 µL of dissolved DNA and TaqMan PCR Core Reagents Kit with AmpliTaq Gold (Applied Biosystems, Tokyo, Japan) were used for a PCR solution. PCR was performed under conditions of 50° C. for 2 minutes (primer annealing)→95° C. for 10 minutes (PCR initial activation)→[95° C. for 20 seconds (denaturation)→60° C. for 1 minute (annealing·extension reaction)]×53 cycles. Reaction was performed using ABI Prism 7500 (Applied Biosystems, Tokyo, Japan). For analysis, each HBV DNA level calculated herein was the average level of the levels found from two wells. In addition, the thus calculated HBV DNA levels of higher than 0 and less than $4.0 \times 10^4$ copies/mL were considered to be PCR positive. The thus calculated HBV DNA levels of 0 were considered to be PCR negative. Specifically, when both the levels found from 2 wells subjected to measurement were PCR positive, the result was denoted as "+" (HBV positive). When both the levels found from two wells were PCR negative, the result was denoted as "−" (HBV negative). When one of the levels found from two wells was positive, the result was denoted as "±" (HBV false-positive).

Primers and a probe used herein had the following sequences.

Forward primer:
(SEQ ID NO: 8)
5-CACATCAGGATTCCTAGGACC-3

Reverse primer:
(SEQ ID NO: 9)
5-AGGTTGGTGAGTGATTGGAG-3

Probe:
(SEQ ID NO: 10)
5-CAGAGTCTAGACTCGTGGTGGACTTC-3
(5'-end: FAM, 3'-end: TAMRA)

As an HBV standard, a plasmid, into which an HBV gene (nucleotides 1 to 2182) had been inserted and the copy number of which had been calculated in terms of the concentration at OD260 nm, was used. The determination limit for the determination of serum HBV DNA ranged from $4.0 \times 10^4$ copies/mL to $4.0 \times 10^9$ copies/mL. Specimens exhibited $4.0 \times 10^9$ copies/mL or more were diluted and then deremination was performed with the measurement range.

Figure 2:
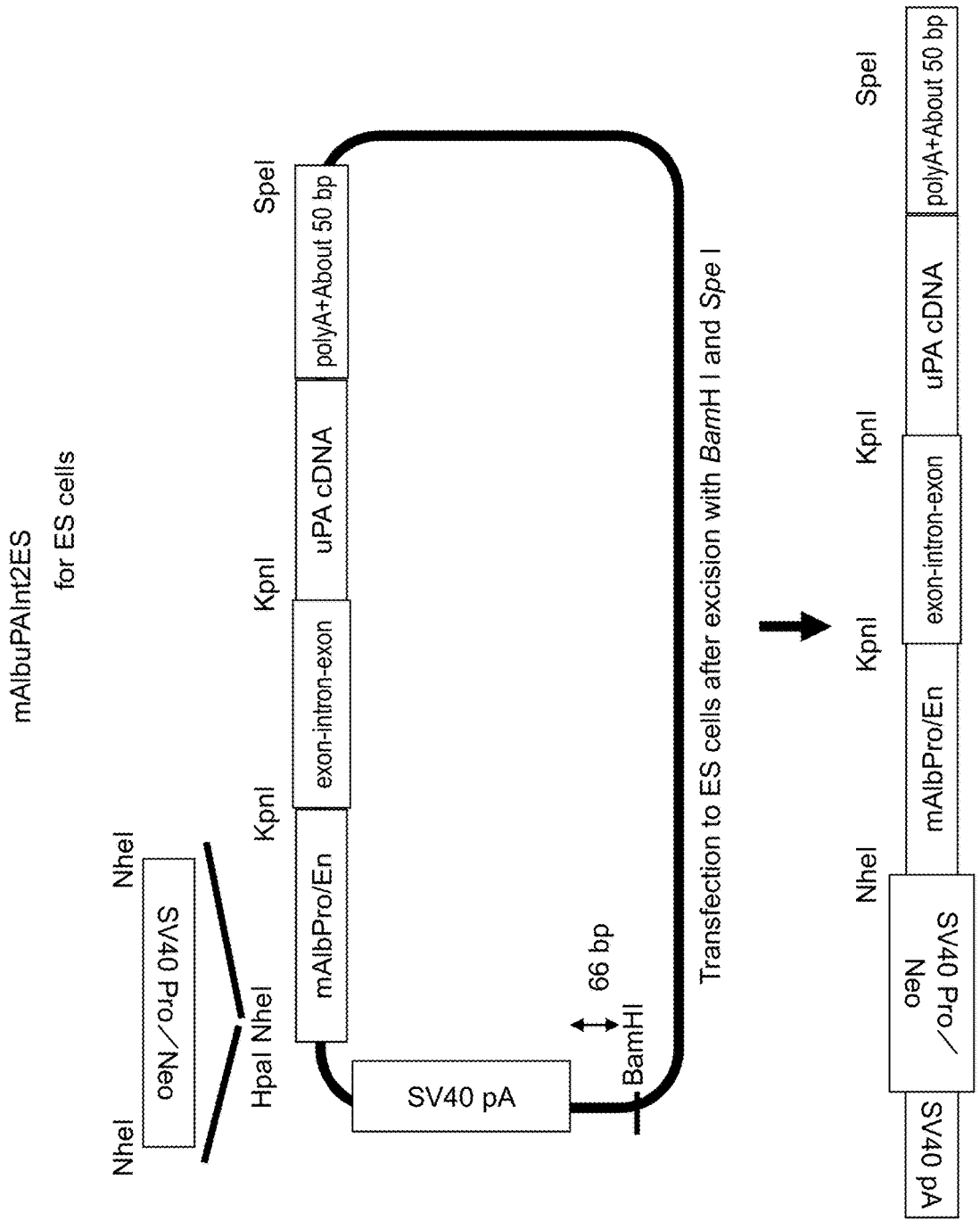
FIG. 2 is a schematic view showing an uPA gene insertion vector for ES cells, "mAlb uPAInt2ES". SV40 pA: SV40 polyA signal; mAlbPro/En: mouse albumin enhancer/promoter; uPA cDNA: the ORF portion of mouse uPA; exon-intron-exon: the $2^{nd}$ exon, intron, and the $3^{rd}$ exon of rabbit β-globin; polyA+About 50 bp: polyA signal in the $3^{rd}$ exon of rabbit β-globin.
Figures 1, 8:
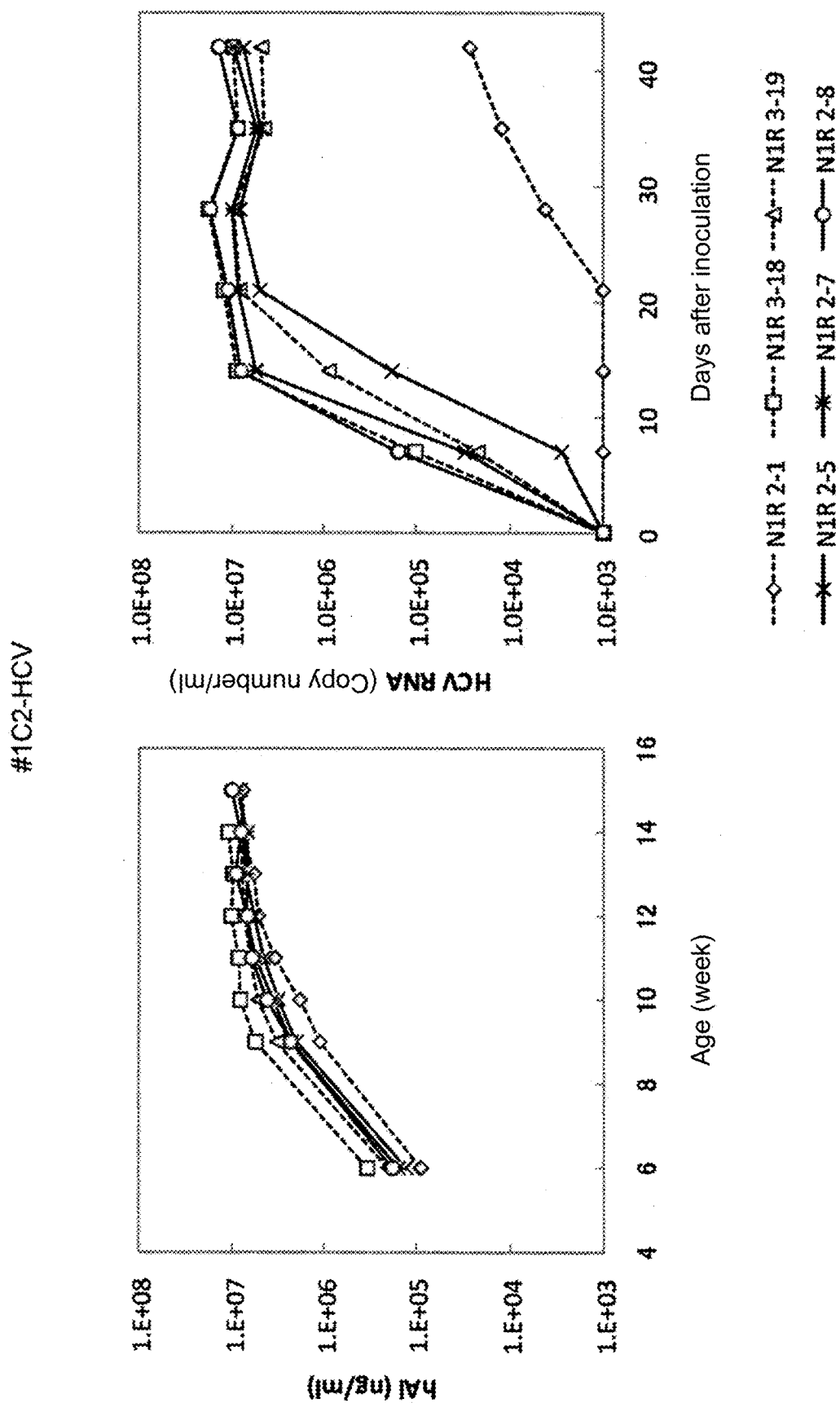
Figures 2, 8:
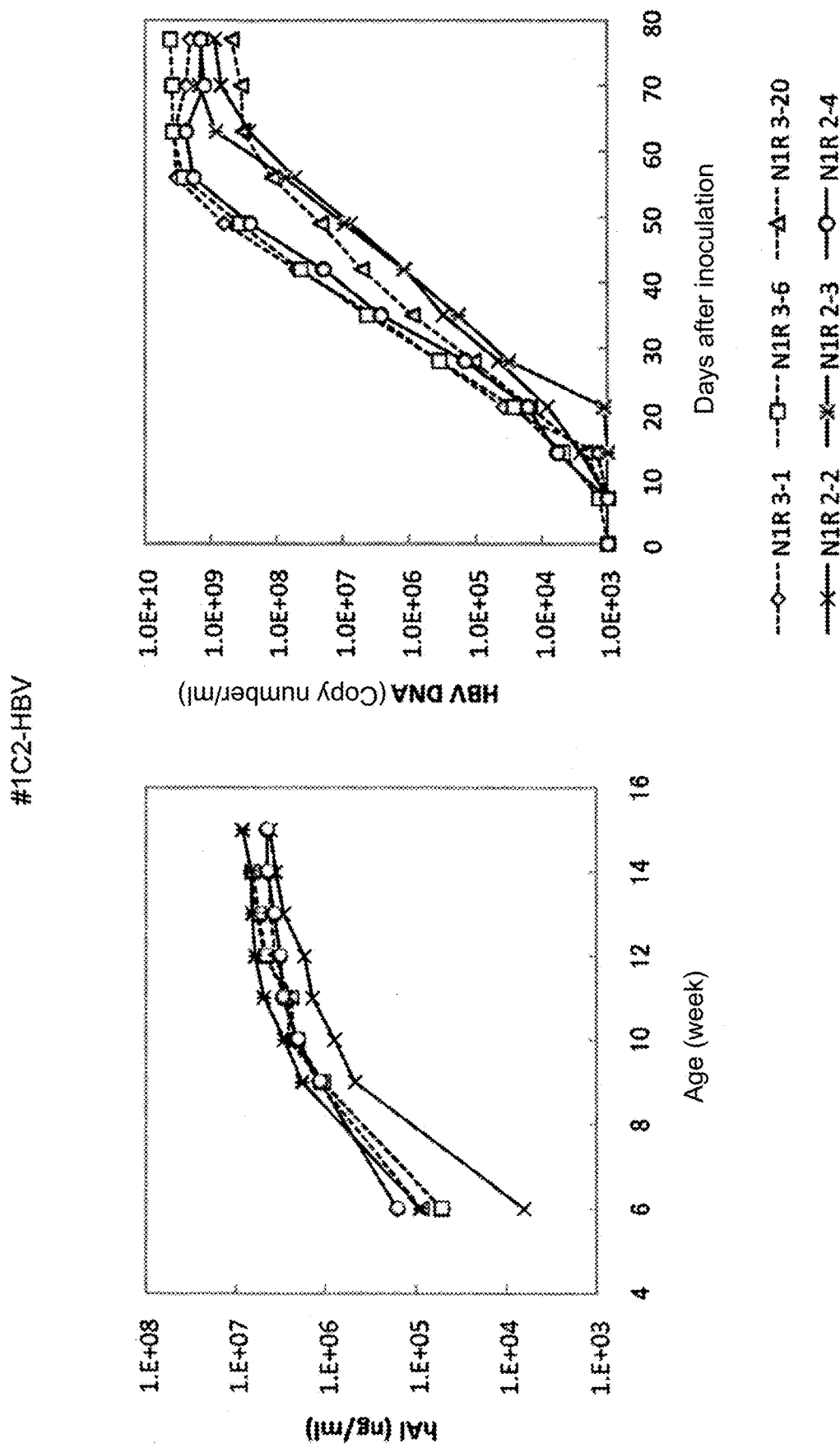
Figures 1, 9:
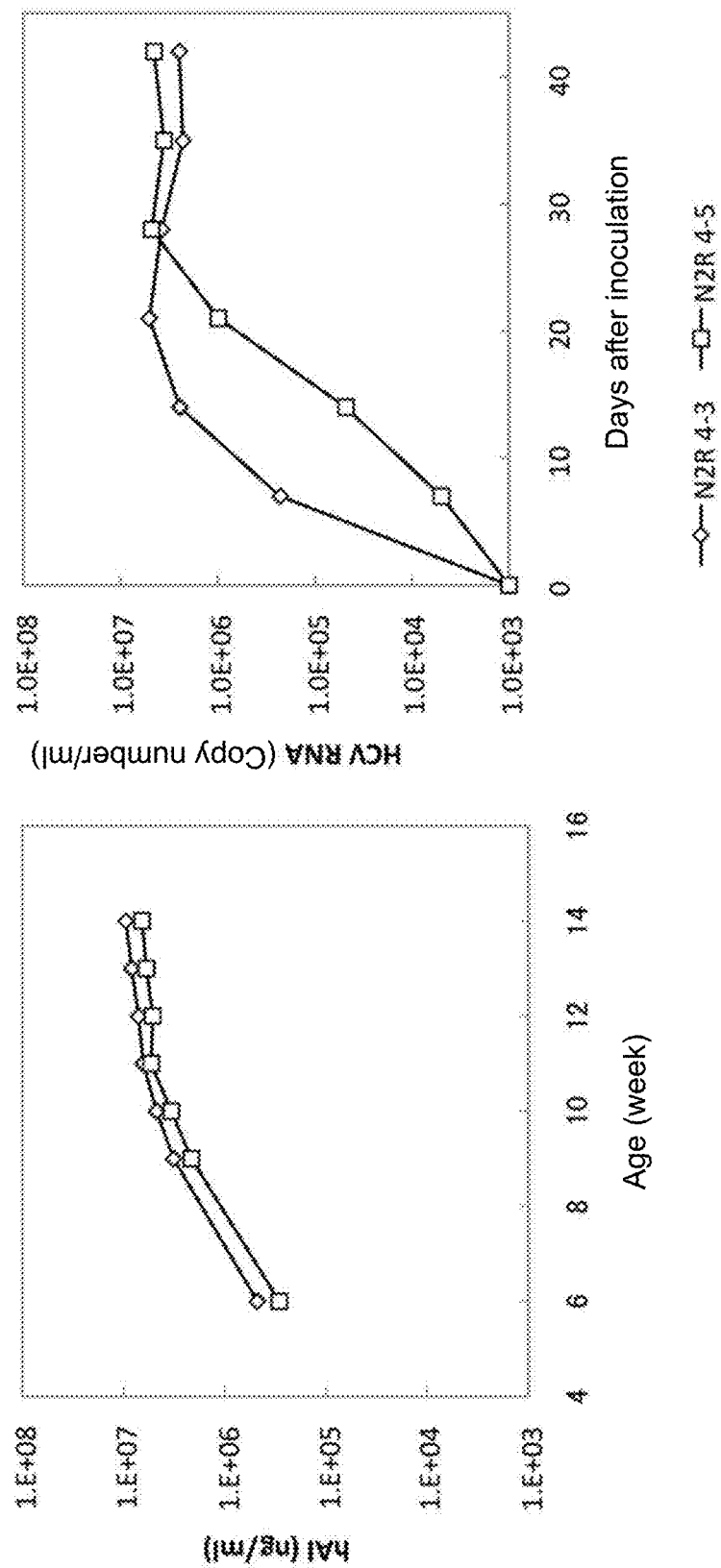
Figures 2, 9:
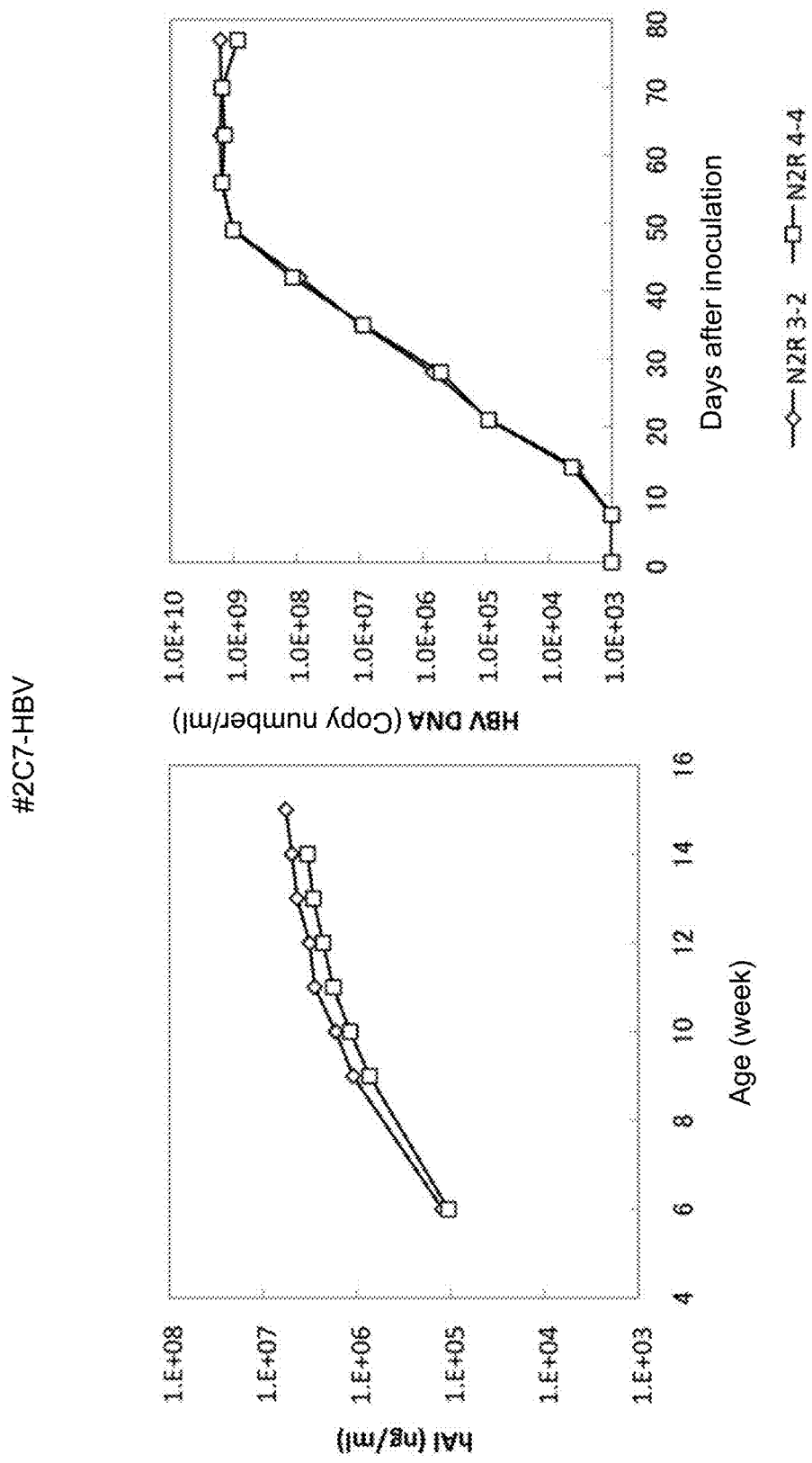

As a result, HBV infection and HCV infection were confirmed for all the infected mice (FIG. 8-1, 2, FIG. 9-1, 2). HCV was detected on week 1 after inoculation for 7 out of 8 cases of HCV-inoculated mice, and the HCV level reached a plateau around week 4 after inoculation (FIG. 8-1, FIG. 9-1). HCV was detected on week 4 after inoculation for 1 out of 8 cases (FIG. 8-1, FIG. 9-1). Regarding HBV, HBV was detected in mouse serum on week 3 after inoculation for 7 out of 8 cases, and all the mice were infected on week 4. The level reached plateau on week 8 after inoculation (FIG. 8-2, FIG. 9-2). In terms of infection efficiency and viral growth rate, no clear difference was confirmed between #1C2 and #2C7, and, between #1C2 heterozygous and #1C2 homozygous mice (FIG. 8-1, 2, FIG. 9-1, 2). In addition, in the case of #2C7 heterozygous mice, chimeric mice having high replacement rates; that is, human albumin concentrations in mouse blood of 7 mg/mL or higher, were not obtained. Hence, none of these mice were used for the infection experiment.

Figure 10:
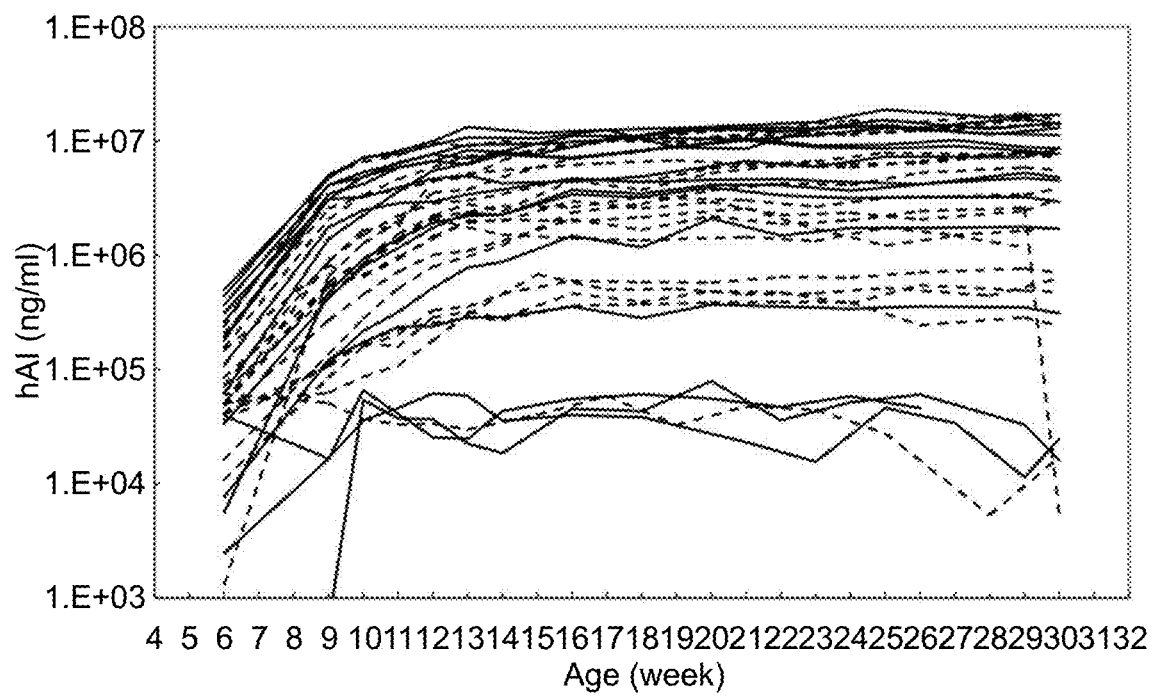
FIG. 10 shows the results of measuring human albumin concentrations in mouse blood (top) and body weights (bottom) of #1C2 mice (up to 30 weeks old) after transplantation of human hepatocytes into the mice. Solid lines denote homozygous mice and dotted lines denote heterozygous mice.
Figure 10:
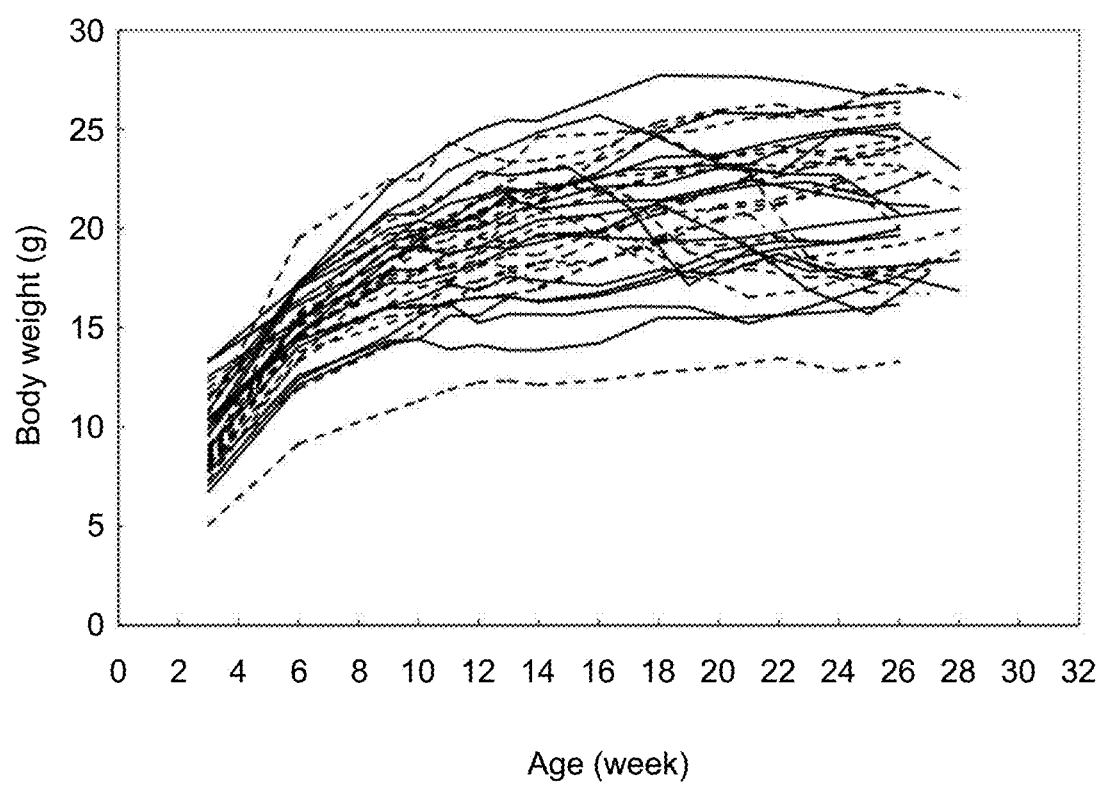
Figure 11:
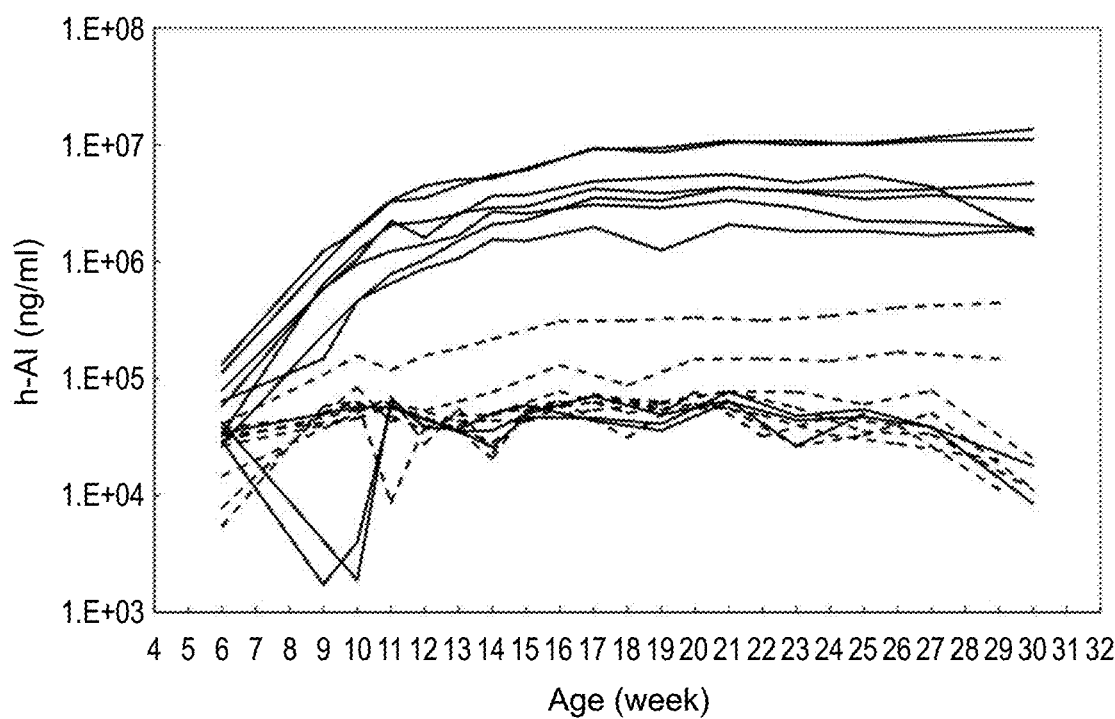
FIG. 11 shows the results of measuring human albumin concentrations in mouse blood (top) and body weights (bottom) of #2C7 mice (up to 30 weeks old) after transplantation of human hepatocytes into the mice. Solid lines denote homozygous mice and dotted lines denote heterozygous mice.
Figure 11:
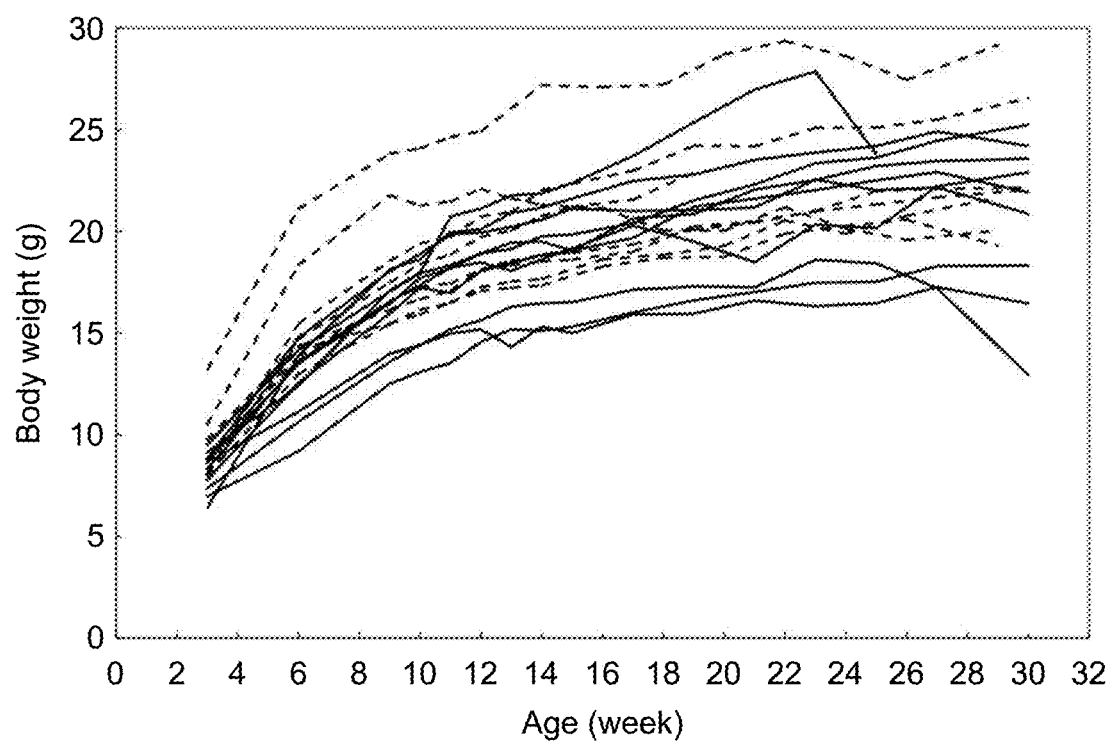

The remaining mice (22 #1C2 homozygous mice, 22 #1C2 heterozygous mice, 14 #2C7 homozygous mice, and 15 #2C7 heterozygous mice) were maintained until they were 30 weeks old. Human albumin concentration was measured once a week. These mice were anatomized on week 30, and the replacement rates in liver were similarly determined. The human albumin concentrations were found to continuously increase even after the mice were 14 weeks old or older (FIG. 10 and FIG. 11). Until week 30, no decrease in human albumin concentration in mouse blood was observed for most of these mice. A correlation between human albumin concentrations and replacement rates was observed at autopsy (FIG. 7).

INDUSTRIAL APPLICABILITY

According to the present invention, mice with liver damage having a high degree of damage against mouse's original hepatocytes, while having the uPA gene in a heterozygous form, and a method for efficiently preparing the mice with liver damage can be provided.

All publications, patents, and patent applications cited herein are incorporated herein by reference in their entirety.

The invention claimed is:

1. A chimeric mouse having a chimeric liver that contains transplanted human hepatocytes, wherein:
the chimeric mouse is an immunodeficient mouse having a uPA gene in a heterozygous form;
the mouse does not exhibit rejection against hepatocytes from a different animal origin;
the human hepatocytes were transplanted in an amount between 1 and 2,000,000 cells;
the blood human albumin concentration is 1 mg/mL or higher;
the uPA gene is in the form of cDNA encoding uPA and linked to a liver specific promoter;
and the blood human albumin concentration increases for at least 10 weeks after transplantation of the human hepatocytes,
wherein the chimeric mouse has a replacement rate of human hepatocytes of 60% or more.

2. The mouse of claim 1, wherein the chimeric mouse was obtained by:
transforming mouse ES cells with a DNA fragment containing a liver-specific promoter/enhancer and cDNA that encodes uPA operably linked under the control thereof;
injecting the transformed mouse ES cells obtained above into a host embryo;
transplanting the host embryo obtained above via the injection of the ES cells into the uterus of a surrogate mother mouse, so as to obtain a chimeric mouse;
crossing the chimeric mice obtained above, so as to obtain a transgenic mouse with liver damage in which the DNA fragment is introduced in a heterozygous form;
crossing the mouse with liver damage with an immunodeficient mouse forming an immunodeficient mouse with liver damage having the uPA gene in a heterozygous form; and
transplanting human hepatocytes into the immunodeficient mouse with liver damage having the uPA gene in a heterozygous form.

3. A chimeric mouse having a chimeric liver that contains transplanted human hepatocytes, wherein the chimeric mouse is an immunodeficient mouse having a uPA gene in a heterozygous form, and the blood human albumin concentration increases for at least 10 weeks after transplantation of human hepatocytes,
wherein the chimeric mouse has a replacement rate of human hepatocytes of 60% or more.

4. The chimeric mouse of claim 3, wherein the mouse does not exhibit rejection against hepatocytes from a different animal origin.

5. The chimeric mouse of claim 3, wherein the blood human albumin concentration is 1 mg/mL or higher.

6. The chimeric mouse of claim 3, wherein the uPA gene is in the form of cDNA encoding uPA and linked to a liver specific promoter.

7. The chimeric mouse of claim 3, wherein the chimeric mouse was obtained by:
- transforming mouse ES cells with a DNA fragment containing a liver-specific promoter/enhancer and cDNA that encodes uPA operably linked under the control thereof;
- injecting the transformed mouse ES cells obtained above into a host embryo;
- transplanting the host embryo obtained above via the injection of the ES cells into the uterus of a surrogate mother mouse, so as to obtain a chimeric mouse;
- crossing the chimeric mice obtained above, so as to obtain a transgenic mouse with liver damage in which the DNA fragment is introduced in a heterozygous form;
- crossing the mouse with liver damage with an immunodeficient mouse forming an immunodeficient mouse with liver damage having the uPA gene in a heterozygous form; and
- transplanting human hepatocytes into the immunodeficient mouse with liver damage having the uPA gene in a heterozygous form.

8. A chimeric mouse having a chimeric liver that contains transplanted human hepatocytes, wherein the chimeric mouse is an immunodeficient mouse having a uPA gene in a heterozygous form and the blood human albumin concentration is 1 mg/mL or higher and the uPA gene is in the form of cDNA encoding uPA, wherein the chimeric mouse has a replacement rate of human hepatocytes of 60% or more.

9. The chimeric mouse of claim 8, wherein the uPA gene is linked to a liver specific promoter.

10. The chimeric mouse of claim 8, wherein the mouse does not exhibit rejection against hepatocytes from a different animal origin.

11. The mouse of claim 8, wherein the chimeric mouse was obtained by:
- transforming mouse ES cells with a DNA fragment containing a liver-specific promoter/enhancer and cDNA that encodes uPA operably linked under the control thereof;
- injecting the transformed mouse ES cells obtained above into a host embryo;
- transplanting the host embryo obtained above via the injection of the ES cells into the uterus of a surrogate mother mouse, so as to obtain a chimeric mouse;
- crossing the chimeric mice obtained above, so as to obtain a transgenic mouse with liver damage in which the DNA fragment is introduced in a heterozygous form;
- crossing the mouse with liver damage with an immunodeficient mouse forming an immunodeficient mouse with liver damage having the uPA gene in a heterozygous form; and
- transplanting human hepatocytes into the immunodeficient mouse with liver damage having the uPA gene in a heterozygous form.

* * * * *

SEQUENCE LISTING

<160> NUMBER OF SEQ ID NOS: 11

<210> SEQ ID NO 1
<211> LENGTH: 36
<212> TYPE: DNA

```
<213> ORGANISM: Artificial
<220> FEATURE:
<223> OTHER INFORMATION: primer

<400> SEQUENCE: 1
gggcggcggt accgatcctg agaacttcag ggtgag                              36

<210> SEQ ID NO 2
<211> LENGTH: 36
<212> TYPE: DNA
<213> ORGANISM: Artificial
<220> FEATURE:
<223> OTHER INFORMATION: primer

<400> SEQUENCE: 2
gggcggcggt accaattctt tgccaaaatg atgaga                              36

<210> SEQ ID NO 3
<211> LENGTH: 36
<212> TYPE: DNA
<213> ORGANISM: Artificial
<220> FEATURE:
<223> OTHER INFORMATION: primer

<400> SEQUENCE: 3
gggcggcggt accgatcctg agaacttcag ggtgag                              36

<210> SEQ ID NO 4
<211> LENGTH: 36
<212> TYPE: DNA
<213> ORGANISM: Artificial
<220> FEATURE:
<223> OTHER INFORMATION: primer

<400> SEQUENCE: 4
gggcggcggt accaattctt tgccaaaatg atgaga                              36

<210> SEQ ID NO 5
<211> LENGTH: 17
<212> TYPE: DNA
<213> ORGANISM: Artificial
<220> FEATURE:
<223> OTHER INFORMATION: primer

<400> SEQUENCE: 5
cgggagagcc atagtgg                                                   17

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6
agtaccacaa ggcctttcg                                                 19

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
ctgcggaacc ggtgagtaca c                                              21
```

-continued

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
cacatcagga ttcctaggac c                                              21

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
aggttggtga gtgattggag                                                20

<210> SEQ ID NO 10
<211> LENGTH: 26
<212> TYPE: DNA
<213> ORGANISM: Artificial
<220> FEATURE:
<223> OTHER INFORMATION: primer

<400> SEQUENCE: 10
cagagtctag actcgtggtg gacttc                                         26

<210> SEQ ID NO 11
<211> LENGTH: 2343
<212> TYPE: DNA
<213> ORGANISM: Mus musculus

<400> SEQUENCE: 11
gtagccccag agctctgtct gtcatccatc cagtccttgc gtgtctgcca gcgcccttcc     60
gctgcagtca ccgaactgct gtctagagcc cagcggcact accatgaaag tctggctggc    120
gagcctgttc ctctgcgcct tggtggtgaa aaactctgaa ggtggcagtg tacttggagc    180
tcctgatgaa tcaaactgtg gctgtcagaa cggaggtgta tgcgtgtcct acaagtactt    240
ctccagaatt cgccgatgca gctgcccaag gaaattccag gggagcact gtgagataga    300 tgcatcaaaa acctgctatc atggaaatgg tgactcttac cgaggaaagg ccaacactga    360
taccaaaggt cggccctgcc tggcctggaa tgcgcctgct gtccttcaga acccctacaa    420
tgcccacaga cctgatgcta ttagcctagg cctggggaaa cacaattact gcaggaaccc    480
tgacaaccag aagcgaccct ggtgctatgt gcagattggc ctaaggcagt ttgtccaaga    540
atgcatggtg catgactgct ctcttagcaa aaagccttct tcgtctgtag accaacaagg    600
cttccagtgt ggccagaagg ctctaaggcc ccgctttaag attgttgggg gagaattcac    660
tgaggtggag aaccagccct ggttcgcagc catctaccag aagaacaagg gaggaagtcc    720
tccctccttt aaatgtggtg ggagtctcat cagtccttgc tgggtggcca gtgccgcaca    780
ctgcttcatt caactcccaa agaaggaaaa ctacgttgtc tacctgggtc agtcgaagga    840
gagctcctat aatcctggag agatgaagtt tgaggtggag cagctcatct gcacgaata    900 ctacagggaa gacagcctgg cctaccataa tgatattgcc ttgctgaaga tacgtaccag    960
cacgggccaa tgtgcacagc catccaggtc catacagacc atctgcctgc ccccaaggtt   1020

```
tactgatgct ccgtttggtt cagactgtga gatcactggc tttggaaaag agtctgaaag    1080
tgactatctc tatccaaaga acctgaaaat gtccgtcgta aagcttgttt ctcatgaaca    1140
gtgtatgcag ccccactact atggctctga aattaattat aaaatgctgt gtgctgcgga    1200
cccagagtgg aaaacagatt cctgcaaggg cgattctgga ggaccgctta tctgtaacat    1260
cgaaggccgc ccaactctga gtgggattgt gagctggggc cgaggatgtg cagagaaaaa    1320
caagcccggt gtctacacga gggtctcaca cttcctggac tggattcaat cccacattgg    1380
agaagagaaa ggtctggcct tctgatggcc ctcaggtagc tgagggaaga aacagatggg    1440
tcacttgttc ccatgctgac cgtcctctct gcaacagagt cgtcaaatgg agggaagaag    1500
ctgaaaagac aggttttgca ttgatcctct gctgtgctgc ccaccagggt gagcgccaat    1560
agcattaccc tcagacacag gcctgggtgc tggccatcca gaccctcccg accaggatgg    1620
aaagttggtc ctgactcagg atgctataga ccaggagttg cctttttatg gactaaagcc    1680
atctgcagtt tagaaaacat ctcctgggca agtgtaggag gagagctgtt tcccttaatg    1740
ggtcattcat gagatctgct gttgggaaat aaatgatttc ccaattagga agtgcaacag    1800
ctgaggtatt gtgagggtgc ttgtccaata tgagaacggt agcttgagga gtagagacac    1860
taacggcttg agggaacagc tctagcatcc catgaatgga tcaggaaatg ttatatttgt    1920
gtgtatgttt gttcactctg cacaggctgt gagtataagc ctgagcaaaa gctggtgtat    1980
ttctgtatct aactgcaagt ctaggtattt ccctaactcc agactgtgat gcggggccat    2040
ttggtcttcc atgtgatgct ccacgtgaat gtatcattcc cgggcgtgac ccgtgactag    2100
cactaaatgt cggtttcact tttatatag atgtccactt cttggccagt tatctttttt    2160
tttttttttt tttttttttt tttttttttt ttactaatta gcctagttca tccaatcctc    2220
actgggtggg gtaaggacca cttctacata cttaatattt aataattatg ttctgctatt    2280
tttatttata tctattttta taattctgag taaaggtgat caataaatgt gatttttctg    2340
aag                                                                  2343
```